US011851407B2

United States Patent
Ravert et al.

(10) Patent No.: US 11,851,407 B2
(45) Date of Patent: *Dec. 26, 2023

(54) SYNTHESIS OF THE RADIOLABELED PROSTATE-SPECIFIC MEMBRANE ANTIGEN (PSMA) INHIBITOR [$^{18}$F]DCFPYL

(71) Applicant: The Johns Hopkins University, Baltimore, MD (US)

(72) Inventors: Hayden T. Ravert, Bel Air, MD (US); Daniel P. Holt, Severna Park, MD (US); Ying Chen, Lutherville-Timonium, MD (US); Ronnie C. Mease, Fairfax, VA (US); Hong Fan, Timonium, MD (US); Martin G. Pomper, Baltimore, MD (US); Robert F. Dannals, Sparks, MD (US)

(73) Assignee: THE JOHNS HOPKINS UNIVERSTY, Baltimore, MD (US)

( * ) Notice: Subject to any disclaimer, the term of this patent is extended or adjusted under 35 U.S.C. 154(b) by 333 days.

This patent is subject to a terminal disclaimer.

(21) Appl. No.: 17/195,895

(22) Filed: Mar. 9, 2021

(65) Prior Publication Data

US 2022/0055991 A1 Feb. 24, 2022

Related U.S. Application Data

(63) Continuation of application No. 16/308,128, filed as application No. PCT/US2017/036681 on Jun. 9, 2017, now Pat. No. 10,947,197.

(60) Provisional application No. 62/348,391, filed on Jun. 10, 2016.

(51) Int. Cl.
| | | |
|---|---|---|
| *C07D 213/42* | (2006.01) | |
| *A61K 51/04* | (2006.01) | |
| *A61P 35/00* | (2006.01) | |
| *C07B 59/00* | (2006.01) | |
| *C07D 213/82* | (2006.01) | |

(52) U.S. Cl.
CPC ........ *C07D 213/42* (2013.01); *A61K 51/0455* (2013.01); *A61K 51/0497* (2013.01); *A61P 35/00* (2018.01); *C07B 59/002* (2013.01); *C07D 213/82* (2013.01)

(58) Field of Classification Search
CPC .... C07D 213/00; C07D 213/42; A61K 51/04; A61P 35/00
See application file for complete search history.

(56) References Cited

U.S. PATENT DOCUMENTS

| 8,778,305 | B2 | 7/2014 | Pomper et al. |
| 9,226,981 | B2 | 1/2016 | Pomper et al. |
| 9,861,713 | B2 | 1/2018 | Pomper et al. |
| 10,500,292 | B2 | 12/2019 | Pomper et al. |
| 2011/0142760 | A1* | 6/2011 | Pomper .................. A61P 9/00 424/1.89 |
| 2019/0177275 | A1 | 6/2019 | Ravert et al. |
| 2020/0282083 | A1 | 9/2020 | Pomper et al. |

FOREIGN PATENT DOCUMENTS

| WO | WO 2006/037950 | 4/2006 |
| WO | WO 2013/173583 | 11/2013 |
| WO | WO 2016/030329 | 3/2016 |

OTHER PUBLICATIONS

Bouvet et al. EJNMMI, 1-15. (Year: 2016).*
Li et al. Tetrahedron Lett, 44, 8113-8115. (Year: 2003).*
Banerjee et al., Synthesis and Evaluation of technetium-99m- and Rhenium-Labeled Inhibitors of the Prostate-Specific Membrane Antigen (PSMA). J Med Chem. Aug. 14, 2008;51(15):4504-17.
Bouvet et al., Automated synthesis of [18F]DCFPyL via direct radiofluorination and validation in preclinical prostate cancer models. EJNMMI Research. 2016; 6:40.
Chen et al., 2-(3-{1-Carboxy-5-[(6-[18F]fluoro-pyridine-3-carbonyl)-amino]-pentyl}-ureido)-pentanedioic Acid, [18F]DCFPyL, a PSMA-based PET Imaging Agent for Prostate Cancer. Clin Cancer Res. Dec. 15, 2011;17(24):7645-53.
Dietlein et al., MComparison of [(18)F]DCFPyL and [(68)Ga]Ga-PSMA-HBED-CC for PSMA-PET Imaging in Patients With Relapsed Prostate Cancer. Mol Imaging Biol. Aug. 2015;17(4):575-84.
Graham et al., Radiofluorinated derivatives of 2-(phosphonomethyl)pentanedioic acid as inhibitors of prostate specific membrane antigen (PSMA) for the imaging of prostate cancer. J Med Chem. Nov. 26, 2012;55(22):9510-20.
International Conference on Harmonisation of Technical Requirements for Registration of Pharmaceuticals for Human Use. ICH Harmonised Tripartite Guideline Impurities: Guideline for Residual Solvents, 1997. 24 pages.
Krasikova, Pet Radiochemistry Automation: State of the Art and Future Trends in 18F-nucleophilic Fluorination, Current Organic Chemistry, 2013; 17(19):2097-2107.
Lazari et al., Fully automated production of diverse 18F-labeled PET tracers on the ELIXYS multi-reactor radiosynthesizer without hardware modification. J Nucl Med Technol. Sep. 2014; 42(3):203-210.
Li et al., Aqueous phosphoric acid as a mild reagent for deprotection of the t-butoxycarbonyl group. Tetrahedron Letters. Oct. 27, 2003;44(44):8113-5.
Li et al., Aqueous Phosphoric Acid as a Mild Reagent for Deprotection of Tert-Butyl Carbamates, Esters, and Ethers. J Org Chem. Nov. 24, 2006;71(24):9045-50.

(Continued)

*Primary Examiner* — Michael G. Hartley
*Assistant Examiner* — Jagadishwar R Samala
(74) *Attorney, Agent, or Firm* — Casimir Jones, S.C.; Jeffrey W. Childers

(57) ABSTRACT

Methods, and related compositions, for the improved synthesis of [$^{18}$F]DCFPyL are disclosed. Also provided are methods, and related compositions, for the use of [$^{18}$F]DCFPyL so produced.

34 Claims, 12 Drawing Sheets

(56) References Cited

OTHER PUBLICATIONS

Maurer et al., Current Use of PSMA-PET in Prostate Cancer Management. Nat Rev Urol. Apr. 2016;13(4):226-35.
Mease et al., N-[N-[(S)-1,3-Dicarboxypropyl]carbamoyl]-4-[18F]fluorobenzyl-L-cysteine, [18F]DCFBC: A New Imaging Probe for Prostate Cancer. Clin Cancer Res. May 15, 2008; 14(10): 3036-3043.
Olberg et al., One step radiosynthesis of 6-[(18)F]fluoronicotinic acid 2,3,5,6-tetrafluorophenyl ester ([(18)F]F-Py-TFP): a new prosthetic group for efficient labeling of biomolecules with fluorine-18. J Med Chem. Feb. 25, 2010;53(4):1732-40.
Ravert et al., An Improved Synthesis of the Radiolabeled Prostate-Specific Membrane Antigen Inhibitor, [(18) F]DCFPyL. J Labelled Comp Radiopharm. Sep. 2016; 59(11):439-450.
Ravert et al., Microwave-assisted radiosynthesis of [18F]ASEM, a radiolabeled α7-nicotinic acetylcholine receptor antagonist. Labelled Comp Radiopharm. Apr. 2015;58(4):180-2.
Ravert et al., A microwave radiosynthesis of the 4-[18F]-fluorobenzyltriphenylphosphonium ion. J Labelled Comp Radiopharm. Oct. 2014;57(12):695-8.
Rowe et al., PSMA-Based [(18)F]DCFPyL PET/CT Is Superior to Conventional Imaging for Lesion Detection in Patients With Metastatic Prostate Cancer. Mol Imaging Biol. Jun. 2016; 18(3): 411-419.
Seigel et al., Cancer Statistics, 2014. CA Cancer J Clin. Jan.-Feb. 2014;64(1):9-29.
Szabo et al., MInitial Evaluation of [(18)F]DCFPyL for Prostate-Specific Membrane Antigen (PSMA)-Targeted PET Imaging of Prostate Cancer. Mol Imaging Biol. Aug. 2015; 17(4): 565-574.
U.S. Pharmacopeia, Chapter <1225> Validation of Compendial Procedues. USP 36-NF31, 2012, pp. 1-5.
U.S. Pharmacopeia, Chapter <823> Radiopharmaceuticals for Positron Emission Tomography—Compounding. USP 32-NF29, 2009, pp. 365-369.
Extended European Search Report for EP17811054.0, dated Oct. 14, 2019, 7 pages.
International Search Report and Written Opinion for PCT/US2017/036681, dated Sep. 18, 2017, 16 pages.
Hayashi, Pot economy and one-pot synthesis. Chem Sci. 2016;7:866-80.
Matsui, Innovative Fully Automated Robotic PET Probe Synthesizer Supported by Global Technology. Isotope News, Dec. 2015, No. 740, 5 pages.

* cited by examiner

SYNTHESIS OF THE RADIOLABELED PROSTATE-SPECIFIC MEMBRANE ANTIGEN (PSMA) INHIBITOR [$^{18}$F]DCFPYL

CROSS-REFERENCE TO RELATED APPLICATIONS

This application is a continuation of U.S. patent application Ser. No. 16/308,128, now allowed, which is a § 371 U.S. National Entry of PCT/US2017/036681, filed Jun. 9, 2017, which claims the benefit of U.S. Provisional Application No. 62/348,391, filed Jun. 10, 2016, each of which is incorporated herein by reference in its entirety.

FEDERALLY SPONSORED RESEARCH OR DEVELOPMENT

This invention was made with government support under CA134675 and CA183031 awarded by the National Institutes of Health. The government has certain rights in the invention.

FIELD OF THE INVENTION

This invention relates to methods, and related compositions, for the improved synthesis of [$^{18}$F]DCFPyL. Also provided are methods, and related compositions, for the use of [$^{18}$F]DCFPyL so produced.

BACKGROUND

With an estimated incidence of over 1 million cases per year and an estimated mortality of 307,000 men per year, prostate cancer is the most common cancer in men and one of the most prevalent cancers worldwide (Mauer, et al., 2016). In the United States alone, there are well over 200 thousand new cases diagnosed annually (Seigel, et al., 2014). Owing in part to serum diagnostic tests for expression of the prostate-specific antigen (PSA) in developing prostate cancer, with proper diagnosis and treatment, the 5-year survival is nearly 99% (seer.cancer.gov).

With greater frequency, the proper diagnosis and monitoring of treatment involves non-invasive molecular imaging. A number of radiotracers for prostate-specific membrane antigen (PSMA) PET imaging for prostate cancer have been developed, including [$^{11}$C]choline, [$^{18}$F]fluorocholine, [$^{68}$Ga]- and [$^{18}$F]-labeled low molecular weight PSMA inhibitors including DCFBC (Mease, et al., 2008) and DCFPyL (Chens, et al., 2011). The successful use of [$^{18}$F]DCFPyL (Chen, et al., 2011; Szabo, et al., 2015) and its favorable distribution and imaging characteristics compared to other PSMA targeting radiotracers (Dietlein, et al., 2015) have led to increased demand for this radiotracer.

SUMMARY OF THE INVENTION

One aspect described herein relates to a method of synthesizing 2-(3-{1-carboxy-5-[(6-[$^{18}$F]fluoro-pyridine-3-carbonyl)-amino]-pentyl}-ureido)-pentanedioic acid ([$^{18}$F]DCFPyL). In certain aspects, the method comprises: (i) radiofluorinating a DCFPyL precursor comprising ester moiety protecting groups to form a radiofluorinated DCPFPyL precursor; (ii) deprotecting the ester moiety protecting groups of the radiofluorinated DCPFPyL precursor of step (i) with phosphoric acid to form [$^{18}$F]DCFPyL in a reaction mixture; and (iii) purifying the [$^{18}$F]DCFPyL from the reaction mixture of step (ii) to provide [$^{18}$F]DCFPyL.

In certain aspects, the protecting groups of the ester moieties of the DCFPyL precursor comprise a protecting group selected from the group consisting of benzyl, p-methoxybenzyl (PMB), tertiary butyl (tert-butyl, or t-butyl), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr). In one particular aspect of any one of the methods described herein, the protecting groups of the ester moieties of a DCFPyL precursor comprise a tert-butyl group.

In one aspect of any one of the methods described herein, the radiofluorination and deprotection can be performed in a single reactor.

The methods of synthesizing [$^{18}$F]DCFPyL as described herein can be performed by manual manipulation or automated control. In one aspect of any of the methods described herein, the synthesis of [$^{18}$F]DCFPyL can be automated by use of a radiofluorination module (RFM) comprising a heating block, syringe pumps (e.g., at least two syringe pumps), a multi-port cap, and valved reagent addition vials. In some aspects, the RFM can further comprise a thermal heating activity. In another aspect of any of the methods described herein, the synthesis of [$^{18}$F]DCFPyL can be automated by use of an ELIXYS automated radiochemistry synthesizer (Sofie Biosciences, Inc., Culver City, Calif.). In some aspects, components of the RFM or ELIXYS automated radiochemistry synthesizer are free of fluorine. Prior to the synthesis, the RFM or ELIXYS automated radiochemistry synthesizer, or reaction portion thereof, can be cleaned with dilute nitric acid, washed with water and dried at 80° C. overnight.

Any known DCFPyL precursor can be used in the radiofluorination step according to the methods described herein. In some aspects of any one of the methods provided herein, the DCFPyL precursor is 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium. In one aspect, the DCFPyL precursor is 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoromethanesulfonate. In another aspect, the DCFPyL precursor is 5-(((S)-6-(tert-butoxy)-5-(3-((S)-1,5-di-tert-butoxy-1,5-dioxopentan-2-yl)ureido)-6-oxohexyl) carbamoyl)-N,N,N-trimethylpyridin-2-aminium trifluoroacetate.

In one aspect of any one of the methods provided herein, the DCFPyL precursor is synthesized by a method comprising coupling of N,N,N-trimethyl-5-((2,3,5,6-tetrafluorophenoxy)carbonyl)-pyridin-2-aminium trifluoromethanesulfonate (compound (2) shown in FIG. 1) and 2-{3-[1-t-butylcarboxylate-(5-aminopentyl)]-uriedo]-di-t-butylpentandioate (compound (1) as shown in FIG. 1). In one aspect of any one of the methods described herein, the DCFPyL precursor is synthesized according to FIG. 1.

In one aspect of any one of the methods provided herein, the DCFPyL precursor is radiofluorinated according to FIG. 5.

In one aspect of any one of the methods provided herein, the {18F}DCFPyL has characteristics meeting the QC Acceptance Specification (2016).

In one aspect of any one of the methods provided herein, the DCFPyL precursor is radiofluorinated by a process comprising: (a) trapping [$^{18}$F]fluoride ion in a cartridge; (b) eluting the cartridge with a solution of a tetrabutylammonium base salt (e.g., tetrabutylammonium hydrogen carbonate (TBABC)) to release the [$^{18}$F]fluoride ion trapped in the cartridge; (c) drying the eluate comprising the [$^{18}$F]fluoride ion to form dried [$^{18}$F]fluoride ion; and (d) adding a solution of DCFPyL precursor (compound (3) as shown in FIG. 5) to the dried [$^{18}$F]fluoride ion.

In one aspect of any one of the methods described herein, the cartridge for trapping [$^{18}$F]fluoride ion is an anion exchange chromatographic cartridge (e.g., Chromafix 30-PS-HCO3 SPE cartridge source). In some aspects of any one of the methods described herein, the cartridge can be pre-conditioned by washing with high purity water prior to trapping [$^{18}$F]fluoride ion in the cartridge.

In some aspects of any one of the methods described herein, the [$^{18}$F]fluoride ion from step (c) is dried. To produce dried [$^{18}$F]fluoride ion, in some aspects, the eluate of (c) comprising the [$^{18}$F] fluoride ion can be dried at a temperature between about 80° C. to about 150° C., e.g., at about 110° C. In some aspects, the eluate of step (c) comprising the [$^{18}$F]fluoride ion can be dried under nitrogen flow. In some aspects, the drying process can last between about 50 seconds to about 300 seconds, or more preferably for 150 seconds. In some aspects, $CH_3CN$ can be added to the dried [$^{18}$F]fluoride ion for further drying.

In one aspect of any one of the methods provided herein, upon addition of the DCFPyL precursor to the dried [$^{18}$F] fluoride ion, the combined solution is heated, e.g., between about 30° C. to about 70° C. In some aspects, the heating can be performed for between about 2 min to about 10 min. In one aspect, the heating is performed at about 50° C. for about 6 min. While heating can be provided by any methods known in the art, in one aspect, the heating is provided by irradiating the combined solution of DCFPyL precursor and the dried [$^{18}$F]fluoride ion with microwave radiation at between about 40 W to about 60 W for between about 20 seconds to about 200 seconds. In one aspect, the heating is provided by irradiating the combined solution of DCFPyL precursor and the dried [$^{18}$F]fluoride ion with microwave radiation at about 50 W for about 30 seconds to about 150 seconds.

After reaction of the DCFPyL precursor with [$^{18}$F]fluoride ion, protecting groups of the ester moieties of the resulting product are deprotected with phosphoric acid. In some aspects of any one of the methods described herein, the deprotection is performed at a temperature of between about 30° C. to about 55° C. In one aspect, the deprotection is performed at a temperature of about 45° C. In some aspects of any one of the methods described herein, the deprotection is performed at a desired temperature for between about 2 mins to about 10 mins.

In some aspects of any one of the methods provided herein, the method further comprises adjusting the pH of the reaction mixture after the deprotecting with phosphoric acid to a pH of between about 2 to about 2.5. Examples of buffers that can be used to adjust the pH of the reaction mixture include, but are not limited to sodium hydroxide and sodium dihydrogen phosphate buffer.

[$^{18}$F]DCFPyL can be purified using any purification and separation methods known in the art. In one aspect of any one of the methods provided herein, [$^{18}$F]DCFPyL is performed by liquid chromatography. For example, [$^{18}$F] DCFPyL can be purified by liquid chromatography using at least one C18 column. In some aspects, a solution comprising [$^{18}$F]DCFPyL is eluted from a first C18 column with a first elution solution comprising methanol and sodium dihydrogen phosphate. An exemplary volume ratio of methanol to sodium hydrogen phosphate is about 15:85. In some aspects, the sodium dihydrogen phosphate can be prepared at a concentration of about 0.01 M (pH 2.1). In one aspect of any one of the methods provided herein, the solution comprising [$^{18}$F]DCFPyL is further subjected to a second C18 column and eluted with a second elution solution comprising alcohol (e.g., ethanol).

In one aspect of any one of the methods provided herein, [$^{18}$F]DCFPyL eluted from the first or second C18 column can be further subjected to filtration. In one aspect, the filtration is performed with a 0.2-μm sterile filter. The filtered [$^{18}$F]DCFPyL can be filtered directly into a sterile vial, which is optionally preloaded with sterile saline.

In some aspects of any one of the methods provided herein, the [$^{18}$F]DCFPyL purification process can be performed in the presence of sodium ascorbate. For example, sodium ascorbate can be added to a collection reservoir and/or in a solution used for eluting the [$^{18}$F]DCFPyL product, e.g., from a C18 column.

In some aspects, the methods of synthesizing [$^{18}$F] DCFPyL described herein provide high quantities of [$^{18}$F] DCFPyL. In one aspect, the yield of [$^{18}$F]DCFPyL after the purifying is at least 20 mCi. In one aspect, the yield of [$^{18}$F]DCFPyL after the purifying is at least 100 mCi. In one aspect, the yield of [$^{18}$F]DCFPyL after the purifying is at least 400 mCi.

Another aspect provided herein relates to a method of radiofluorinating a DCFPyL precursor, which comprises: (i) trapping [$^{18}$F]fluoride ion in a cartridge; (ii) eluting the cartridge with a solution of tetrabutylammonium hydrogen carbonate (TBABC) to release the [$^{18}$F]fluoride ion trapped in the cartridge; (iii) drying the eluate comprising the [$^{18}$F]fluoride ion from step (ii); (iv) adding a solution of DCFPyL precursor (e.g., compound (3) as shown in FIG. 5) to the [$^{18}$F]fluoride ion from step (iii); and (v) heating the combined solution of step (iv).

In one aspect of any one of the methods described herein, the cartridge for trapping [$^{18}$F]fluoride ion is an anion exchange chromatographic cartridge (e.g., Chromafix 30-PS-HCO3 SPE cartridge). In some aspects of any one of the methods described herein, the cartridge can be pre-conditioned by washing with high purity water prior to trapping [$^{18}$F]fluoride ion in the cartridge.

In some aspects of any one of the methods described herein, the [$^{18}$F]fluoride ion from (c) is dried. To produce dried [$^{18}$F]fluoride ion, in some aspects, the eluate of (c) comprising the [$^{18}$F] fluoride ion can be dried at a temperature of between about 80° C. to about 150° C., e.g., at about 110° C. In some aspects, the eluate of (c) comprising the [$^{18}$F]fluoride ion can be dried under nitrogen flow. In some aspects, the drying process can last for between about 50 seconds to about 300 seconds, or more preferably for about 150 seconds. In some aspects, $CH_3CN$ can be added to the dried [$^{18}$F]fluoride ion for further drying.

In one aspect of any one of the methods provided herein, upon addition of the DCFPyL precursor to the dried [$^{18}$F] fluoride ion, the combined solution is heated, e.g., at between about 30° C. to about 70° C. In some aspects, the heating can be performed for between about 2 min to about 10 min. In one aspect, the heating is performed at about 50° C. for about 6 min. While heating can be provided by any methods known in the art, in one aspect, the heating is provided by irradiating the combined solution of DCFPyL precursor and the dried [$^{18}$F]fluoride ion at between about 40 W to about 60 W for between about 20 seconds to about 200 seconds. In one aspect, the heating is provided by microwave irradiating the combined solution of DCFPyL precursor and the dried [$^{18}$F]fluoride ion with microwave radiation at about 50 W for between about 30 seconds to about 150 seconds.

Compositions comprising [$^{18}$F]DCFPyL produced by any one of the methods described herein provided. In one aspect of any one of the compositions described herein, the [$^{18}$F] DCFPyL has an average specific activity of at least about 50 Ci/μmole. In one aspect of any one of the compositions described herein, the [$^{18}$F]DCFPyL has an average specific activity of at least about 50 Ci/μmole or at least about 100 Ci/μmole.

In some aspects of any one of the compositions described herein, the radiochemical purity of [$^{18}$F]DCFPyL ranges from about 95% to about 100%. In some aspects of any one of the compositions described herein, the composition comprises acetonitrile at a concentration of no more than about 400 ppm. In some aspects of any one of the compositions described herein, the composition comprises methanol at a concentration of no more than about 3,000 ppm. In some aspects of any one of the compositions described herein, the composition comprises methanol at a concentration of no more than about 50 ppm.

In one aspect of any one of the compositions described herein, the composition does not comprise one or more cryptands, e.g., one or more Kryptofix® compounds. In one aspect of any one of the compositions described herein, the composition does not comprise triethylamine. In one aspect of any one of the compositions described herein, the composition does not comprise t-butanol.

Also provided herein are kits comprising any one of the compositions as described herein.

Kits comprising a DCFPyL precursor and a reagent for use in radiosythesis of [$^{18}$F]DCFPyL provided herein. In one aspect, the kit comprises a DCFPyL precursor and phosphoric acid. Another aspect provides a kit comprising a DCFPyL precursor and tetrabutylammonium hydrogen carbonate.

In some aspects of any one of the kits provided herein, the DCFPyL precursor is 5-(((S)-6-(tert-butoxy)-5-(3-((S)-1,5-di-tert-butoxy-1,5-dioxopentan-2-yl)ureido)-6-oxohexyl) carbamoyl)-N,N,N-trimethylpyridin-2-aminium. In one aspect, the DCFPyL precursor is 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoromethanesulfonate. In another aspect, the DCFPyL precursor is 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoroacetate.

In one aspect of any one of the kits provided herein, the kit comprises a DCFPyL precursor and instructions for radiolabeling according to any one of the methods provided herein.

In one aspect of any one of the kits provided herein, the kit comprises a DCFPyL precursor and a QC Acceptance Specification (2016) for the [18F]DCFPyL.

In one aspect of any one of the kits provided herein, the kit does not comprise one or more cryptands, e.g., one or more Kryptofix® compounds. In one aspect of any one of the kits provided herein, the kit further comprises [$^{18}$F]fluoride ion, e.g., [$^{18}$F]fluoride ion packaged in a radiation-resistant container.

The compositions and/or kits described herein can be used for imaging, e.g., diagnostic imaging. Accordingly, a method of imaging comprising contacting cells, organs or tissues with any aspect of the compositions is provided herein.

In another aspect, a method of administering to a subject a composition of any aspect of the compositions is provided herein. For example, the method can be used for imaging and/or for treating cancer.

Also within the scope of the present disclosure are (i) an apparatus comprising a radiofluorination module (RFM) or ELIXYS automated radiochemistry synthesizer as described herein; and (ii) an apparatus comprising a radiofluorination module (RFM) or ELIXYS automated radiochemistry synthesizer in which any one of the methods as described herein can be performed.

Certain aspects of the presently disclosed subject matter having been stated hereinabove, which are addressed in whole or in part by the presently disclosed subject matter, other aspects will become evident as the description proceeds when taken in connection with the accompanying Examples and Figures as described herein below.

BRIEF DESCRIPTION OF THE FIGURES

Figure 1:
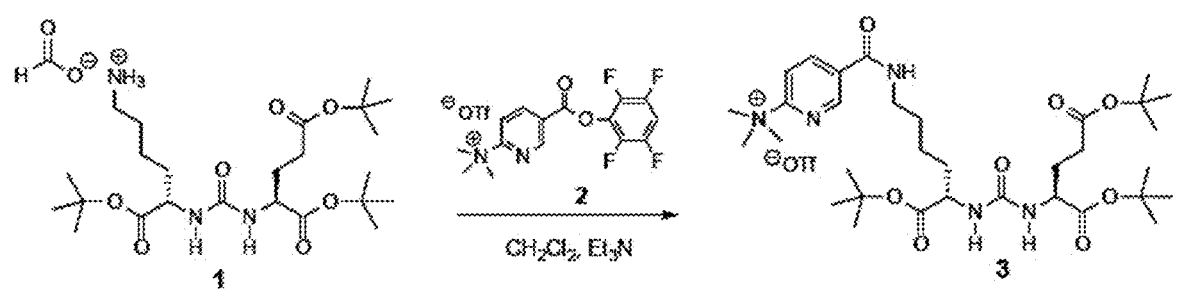
Figure 2A:
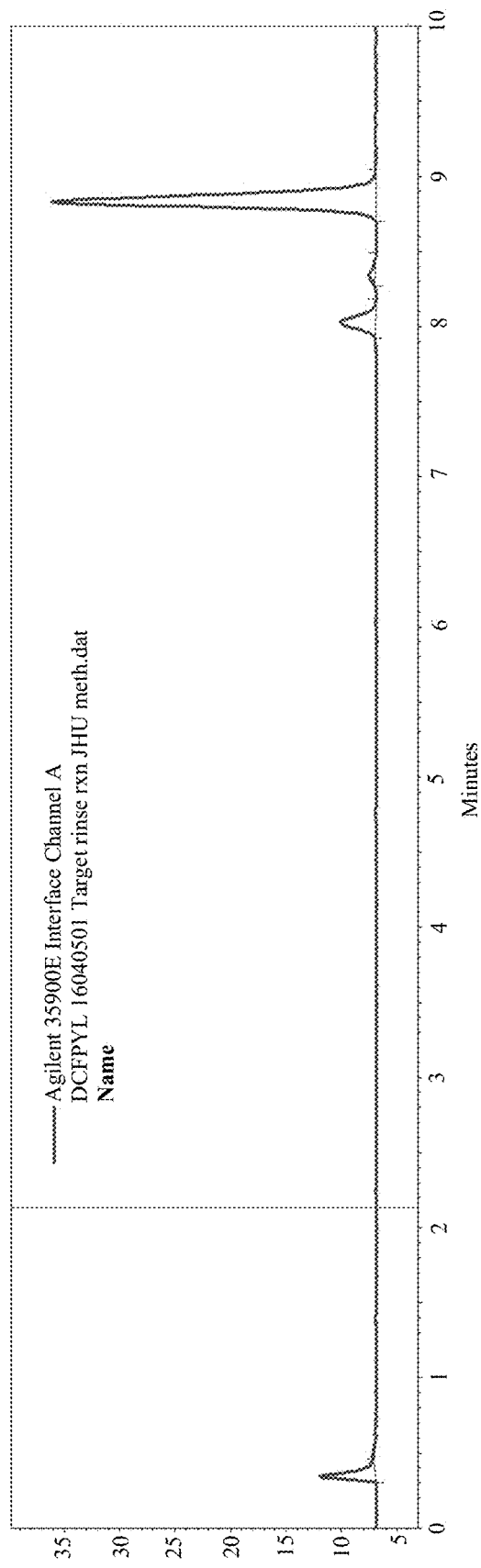
Figure 2B:
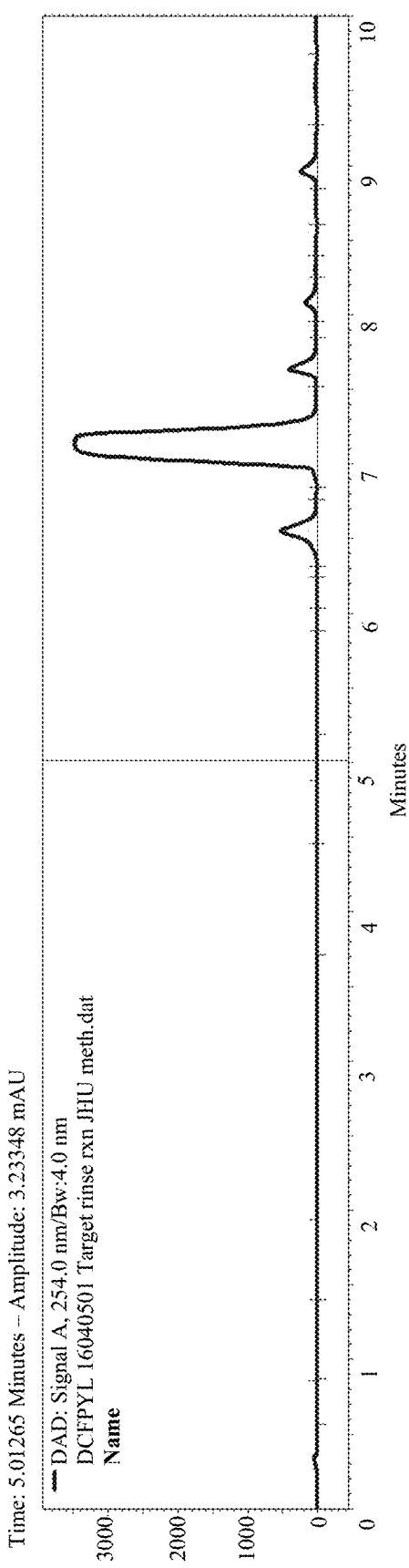
Figure 3:
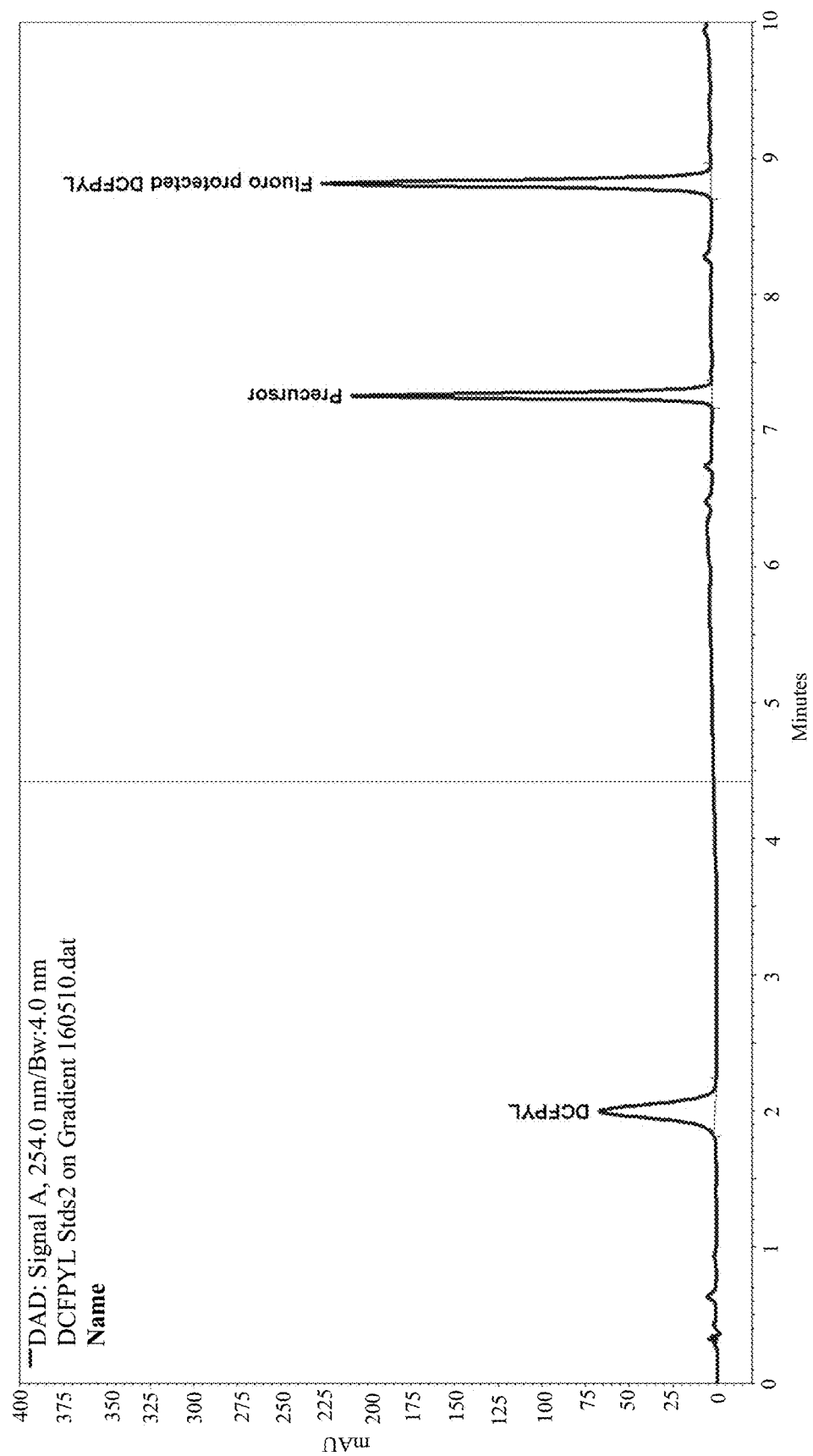
Figure 4:
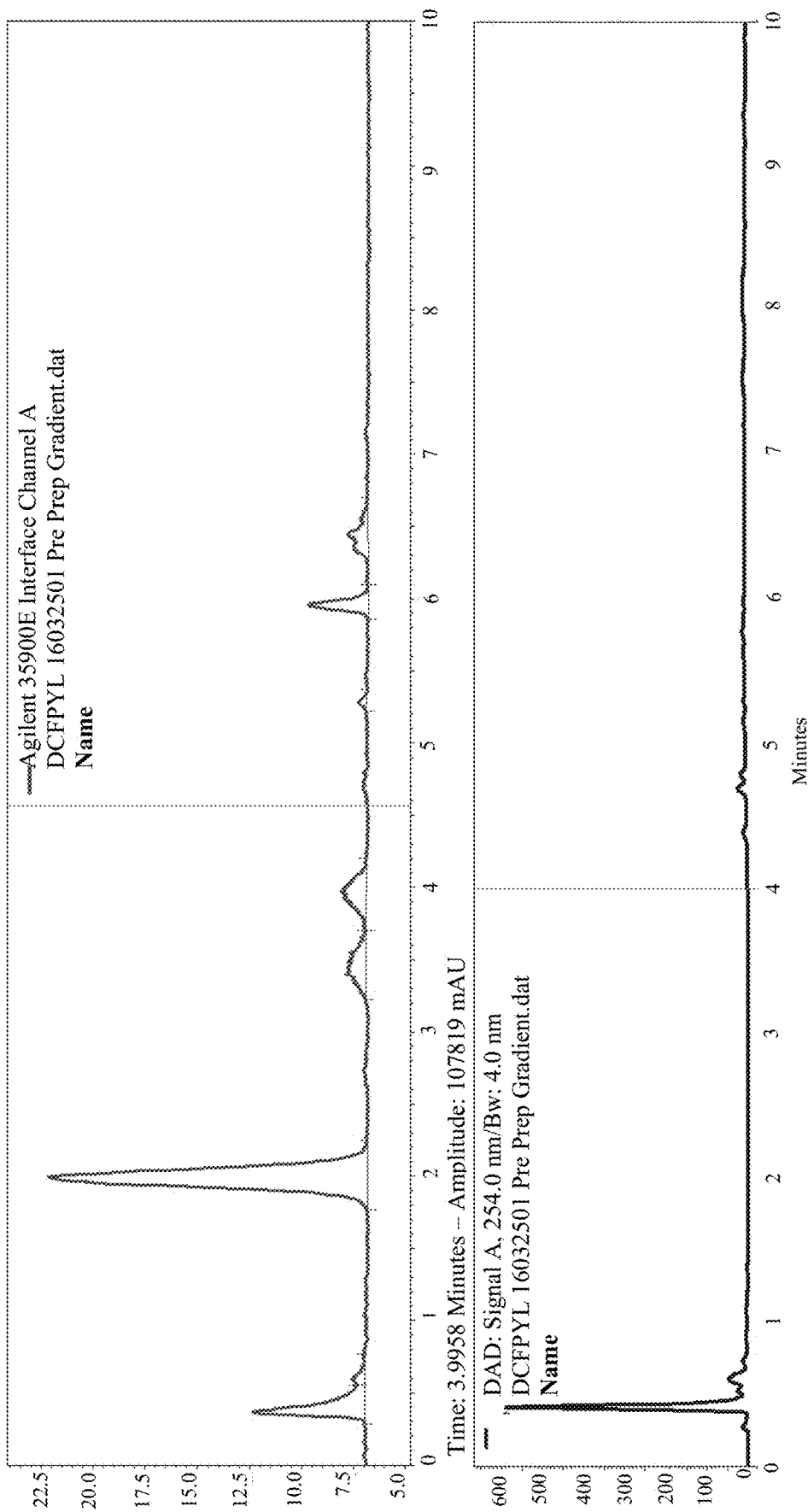
Figure 5:
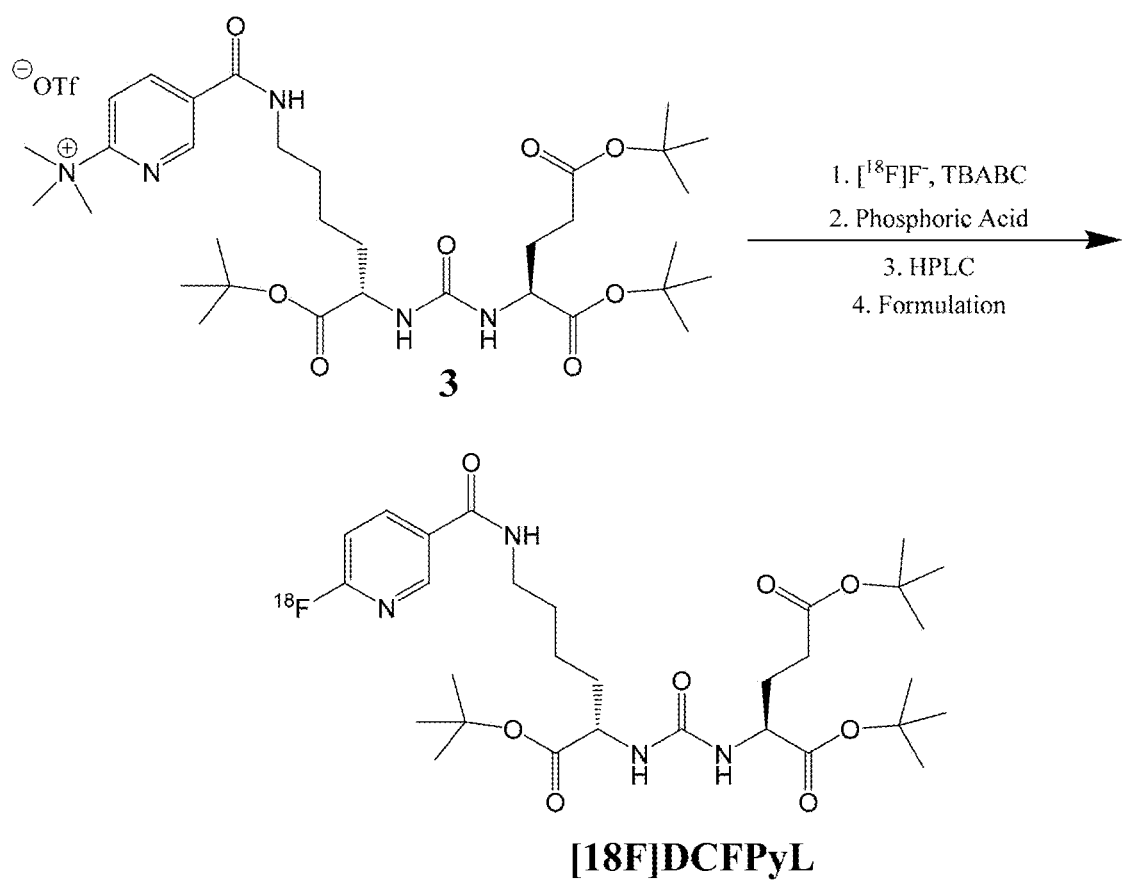
Figure 6A:
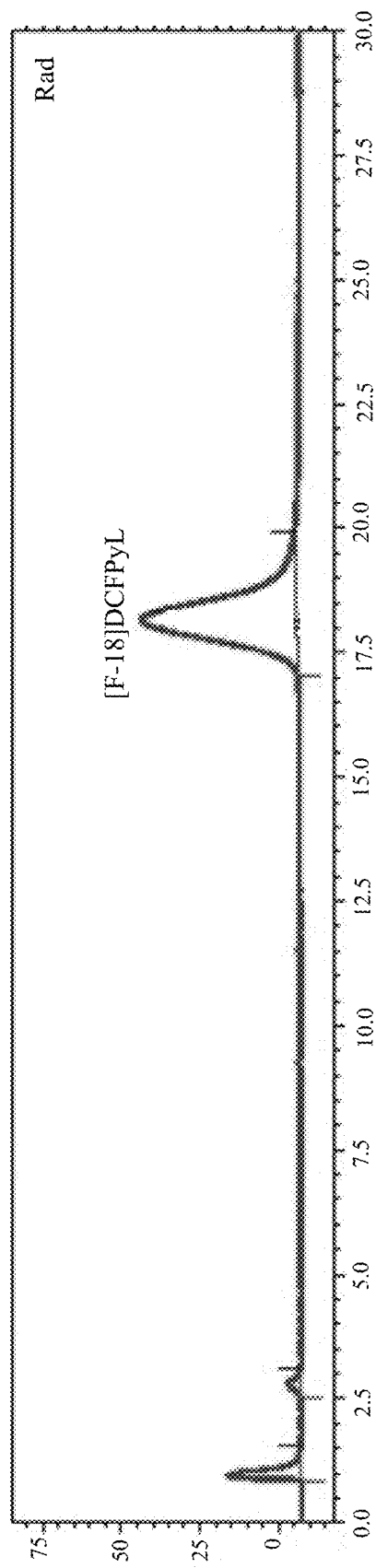
Figure 6B:
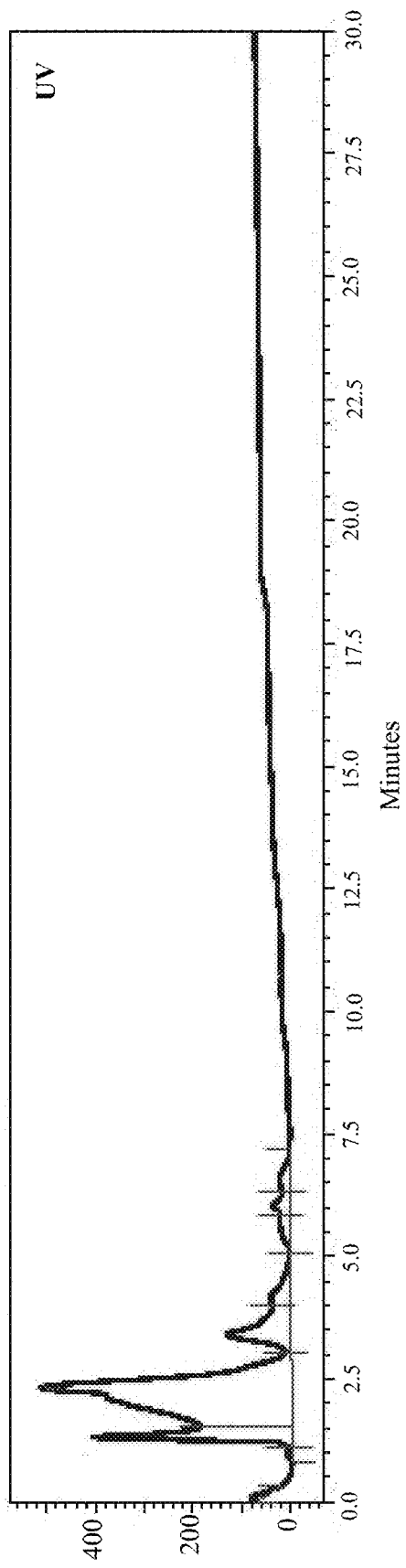
Figure 7A:
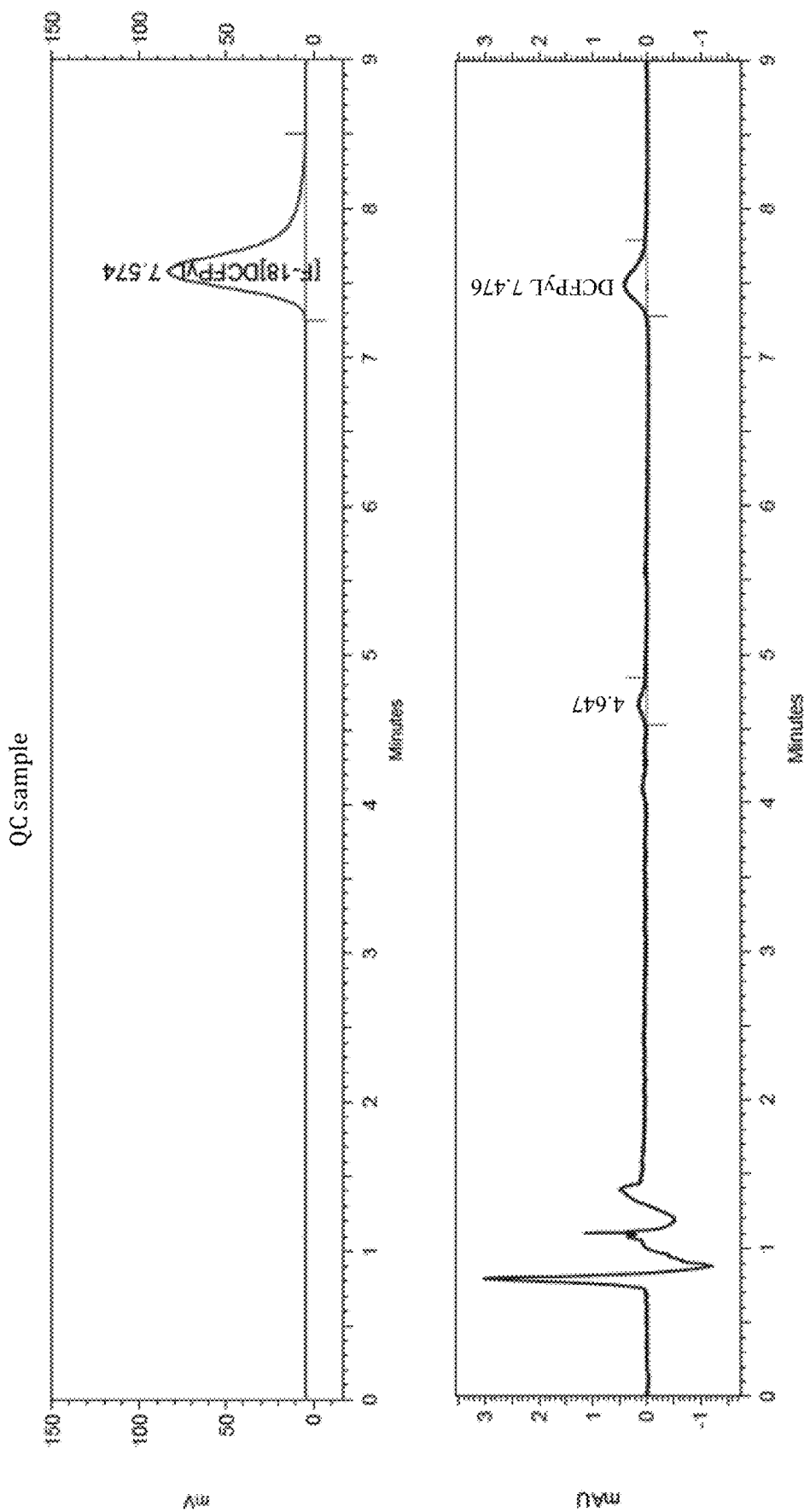
Figure 7B:
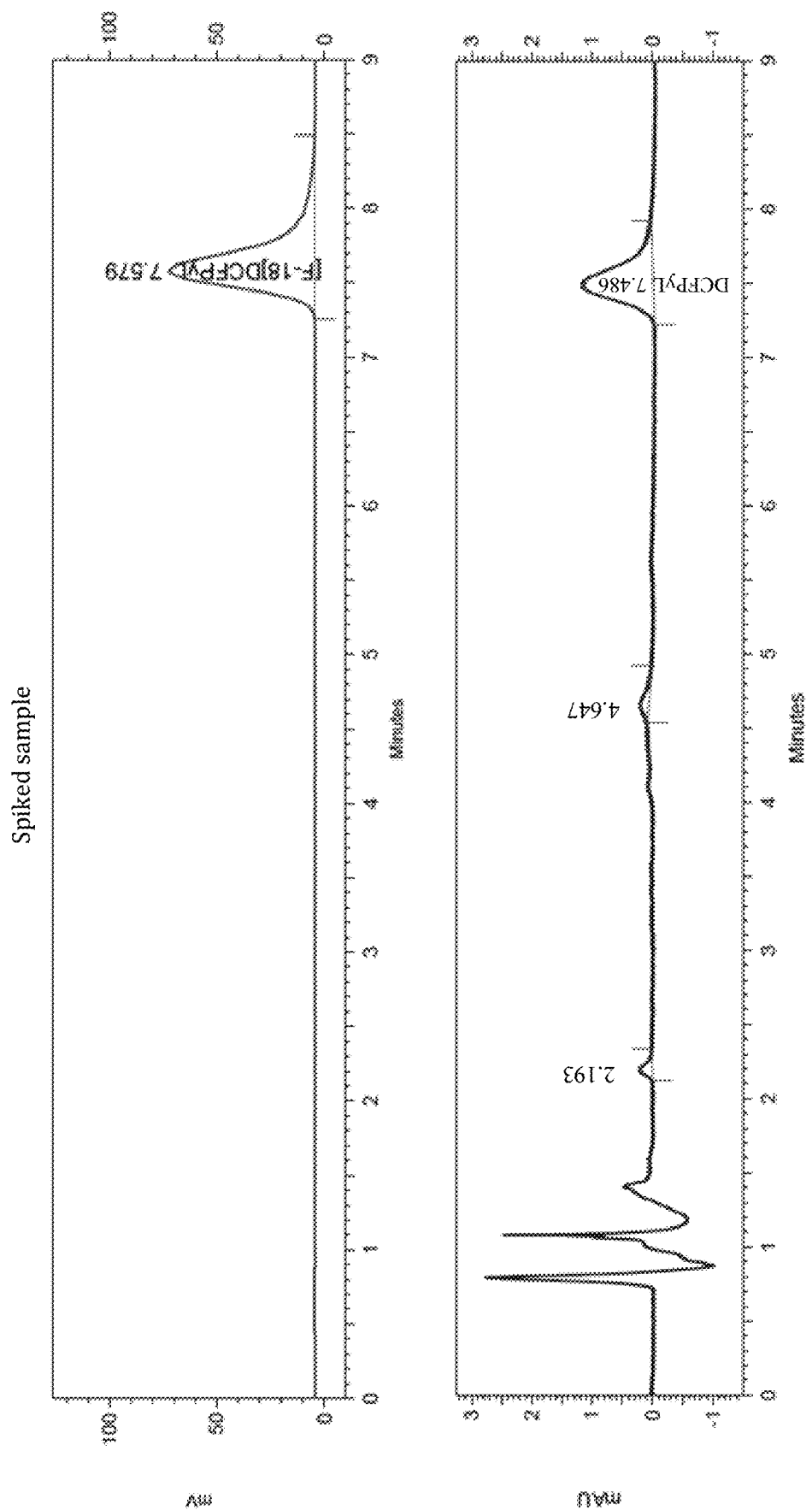
Figure 8A:
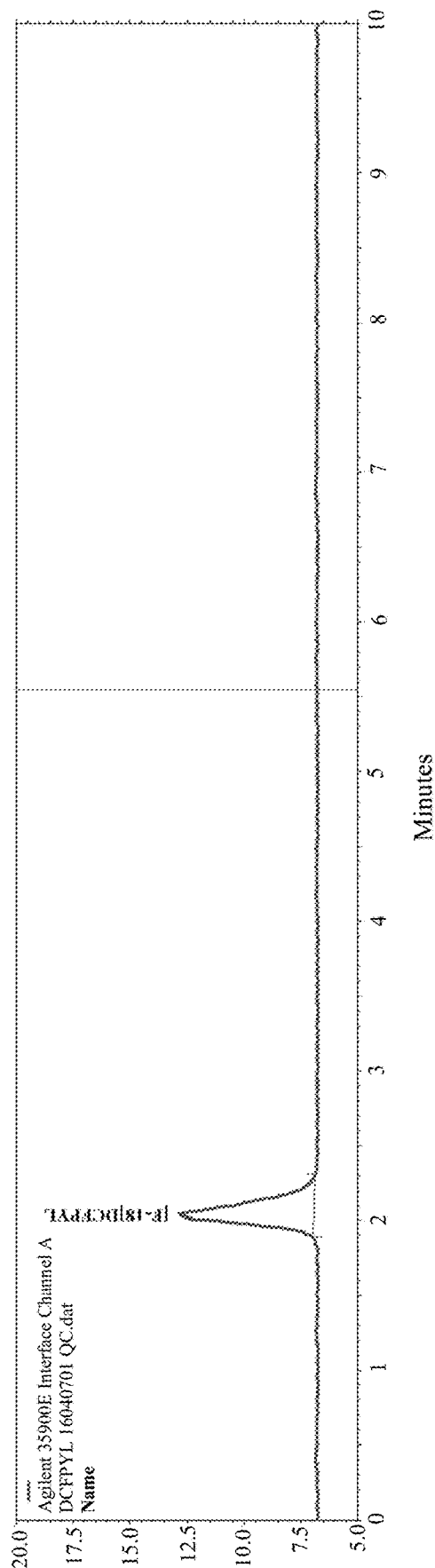
Figure 8B:
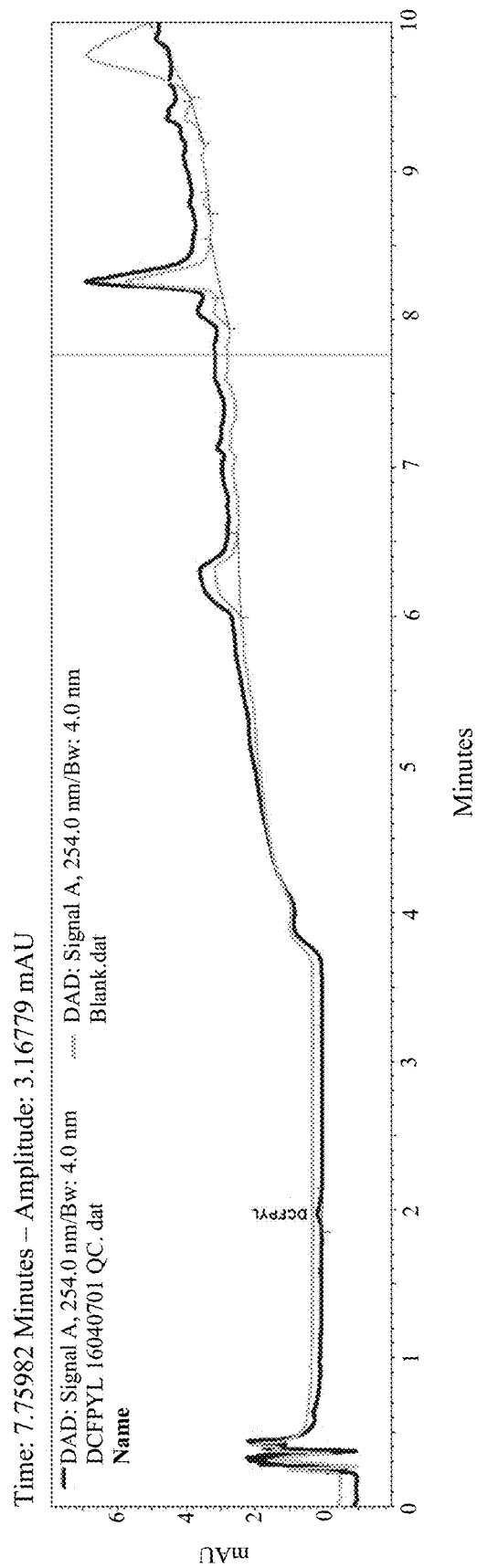

Having thus described the presently disclosed subject matter in general terms, reference will now be made to the accompanying Figures, which are not necessarily drawn to scale, and wherein:

FIG. 1 is a scheme showing the synthesis of the DCFPyL precursor, 5-(((S)-6-(tert-butoxy)-5-(3-((S)-1,5-di-tert-butoxy-1,5-dioxopentan-2-yl)ureido)-6-oxohexyl)carbamoyl)-N,N,Ntrimethylpyridin-2-aminium trifluoromethanesulfonate (3);

FIG. 2A and FIG. 2B shows the gradient HPLC of the [$^{18}$F]t-butyl protected DCFPyL (FIG. 2A—radioactivity, FIG. 2B—UV);

FIG. 3 shows the gradient UV HPLC of DCFPyL, trimethylammonium precursor and fluoroprotected intermediate standards;

FIG. 4 shows the gradient HPLC of the final crude [$^{18}$F]DCFPyL prior to preparative purification;

FIG. 5 is a scheme showing the radiosynthesis of [$^{18}$F] DCFPyL;

FIG. 6A and FIG. 6B show the radioactivity (FIG. 6A) and UV (FIG. 6B) chromatograms of the preparative HPLC of [$^{18}$F]DCFPyL;

FIG. 7A shows a QC chromatogram of [$^{18}$F]DCFPyL. A mass of 0.0134 nmoles for the carrier DCFPyL;

FIG. 7B shows a carrier added chromatogram of [$^{18}$F] DCFPyL. Addition of a standard solution of DCFPyL increases the mass to 0.0384 nmoles; and FIG. 8A and FIG. 8B show gradient HPLC chromatograms of the final formulated [$^{18}$F]DCFPyL. FIG. 8B presents the UV trace of the final product in blue and an overlay of a blank injection of saline in grey to show the gradient trace with no final product present.

DETAILED DESCRIPTION

The presently disclosed subject matter now will be described more fully hereinafter with reference to the accompanying Figures, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

The presently disclosed subject matter provides the preparation of [$^{18}$F]DCFPyL by a multistep synthesis involving the radiofluorination of a prosthetic group and coupling to an urea using an automated radiochemical synthesis module. Along with removing protective ester groups and purification, the automated synthesis of this tracer involves two reactors, multiple individual synthesis steps utilizing two precursors, 90 min of synthesis time, and produces a final product of low to moderate radiochemical yield.

Accordingly, provided herein are improved methods for synthesizing [$^{18}$F]DCFPyL with an increased radiochemical yield, such as from a single precursor with an automated synthesis. Related compositions contemplated herein as are methods of use of [$^{18}$F]DCFPyL produced with the methods provided. The methods provided have been found to result in compositions of [$^{18}$F]DCFPyL with high specific activity.

It also is contemplated that the methods of synthesis of [$^{18}$F]DCFPyL described herein can be applied to radiolabeling a DCFPyL precursor with a different halogen-based radioisotope.

Synthesis of [$^{18}$F]DCFPyL

In some embodiments, the PMSA inhibitor [$^{18}$F]DCFPyL can be synthesized by radiofluorination of a single DCFPyL precursor, 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoromethanesulfonate (3, structure shown in FIG. 5), followed by deprotection of t-butyl groups, and subsequent purification.

Preferably, the methods provided comprise: (i) radiofluorinating a DCFPyL precursor comprising ester moiety protecting groups to form a radiofluorinated DCPFPyL precursor; (ii) deprotecting the ester moiety protecting groups of the radiofluorinated DCPFPyL precursor of step (i) with phosphoric acid to form [$^{18}$F]DCFPyL in a reaction mixture; and (iii) purifying the [$^{18}$F]DCFPyL from the reaction mixture of step (ii) to provide [$^{18}$F]DCFPyL. In some embodiments, the radiofluorination and deprotection steps to form [$^{18}$F]DCFPyL are performed in one reactor or one pot.

In some embodiments, the DCFPyL precursor is a compound of formula (I) or a salt thereof:

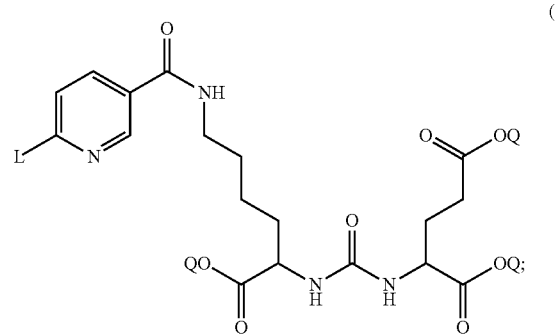

wherein Q is a protecting group of an ester moiety that is removable by treatment of phosphoric acid. As used herein, a "protecting group" is a chemical substituent which can be selectively removed by readily available reagents which do not attack the regenerated functional group or other functional groups in the molecule. Suitable protecting groups may be found, for example in Wutz et al. ("Greene's Protective Groups in Organic Synthesis, Fourth Edition," Wiley-Interscience, 2007). Protecting groups for protection of an ester moiety, as described by Wutz et al. (pages 533-643), are used in certain embodiments. Specific examples of protecting groups include but are not limited to, benzyl, p-methoxybenzyl (PMB), tertiary butyl (tert-butyl, or t-butyl), methoxymethyl (MOM), methoxyethoxymethyl (MEM), methylthiomethyl (MTM), tetrahydropyranyl (THP), tetrahydrofuranyl (THF), benzyloxymethyl (BOM), trimethylsilyl (TMS), triethylsilyl (TES), t-butyldimethylsilyl (TBDMS), and triphenylmethyl (trityl, Tr); and wherein L is a chemical moiety or a leaving group that permits the DCFPyL precursor combined with [$^{18}$F]fluoride ion to form [$^{18}$F]DCFPyL via nucleophilic heteroaromatic substitution reaction. In some embodiments, L can be a positive charge of an atom or a group of atoms. In some embodiments, L is tri($C_1$-$C_6$ alkyl)ammonium (e.g., trimethyl ammonium), with a suitable counterion selected from those derived from mineral acids, for example hydrochloric, hydrobromic, phosphoric, metaphosphoric, perchloric acid, nitric, and sulphuric acids, and those derived from organic acids, for example tartaric, trifluoroacetic, citric, malic, lactic, fumaric, benzoic, glycollic, gluconic, succinic, methanesulphonic, trifluoromethanesulphonic, and para-toluenesulphonic acids; preferably selected from chloride, bromide, perchlorate, sulphonate, nitrate, phosphate, and trifluoromethanesulphonate, more preferably with a trifluoromethanesulphonate counterion.

In some embodiments, the DCFPyL precursor has the structure (I) as shown above with Q being tert-butyl.

In some embodiments, the DCFPyL precursor has the structure (I) as shown above with L being $N^+(CH_3)_3$ or trimethyl ammonium salt.

In some embodiments, the DCFPyL precursor has the structure (I) as shown above with Q being tert-butyl and L being $N^+(CH_3)_3$ or trimethyl ammonium salt.

As used herein, the term "deprotecting" refers to removal of a protecting group of an ester moiety wherein a carbonyl group is formed.

Radiofluorination Modules

Radiofluorination modules are systems for radiofluorinating a compound. They can be automated and remotely controlled to perform radiofluorination to minimize radiation exposure. For example, a radiofluorination module can comprise a plurality of different sub-modules, each sub-module being configured to perform a step of the methods of synthesis of [$^{18}$F]DCFPyL as described herein. In some embodiments, a radiofluorination module can comprise a first sub-module to prepare dried [$^{18}$F]fluoride ion for radiofluorination, a second sub-module to perform radiosynthesis of [$^{18}$F]DCFPyL from a DCFPyL precursor, and a third sub-module to purify the [$^{18}$F]DCFPyL from the radiosynthesis reaction mixture. Each sub-module can be operatively connected, e.g., by connecting tubes and/or pumps. In some embodiments, a radiofluorination module can further comprise a sub-module to produce [$^{18}$F]fluoride ion, which can be received by the first sub-module to prepare dried [$^{18}$F] fluoride ion for radiofluorination.

In some embodiments, the radiofluorination modules can be further configured to include on-line sensors (e.g., for temperature, pressure, flow rates, and radioactivity) to monitor the reaction condition. In some embodiments, the radiofluorination modules can be further configured to include an online analyzer downstream or upstream of a sub-module to monitor quality of the reaction product after each step.

In some embodiments, [$^{18}$F]DCFPyL is synthesized using a custom-made radiofluorination module (RFM). In some embodiments, the RFM hardware comprises a heating block, two syringe pumps, such as two Tecan Carvro syringe pumps, a multi-port cap, such as one constructed for standard v-vials, and valved reagent addition vials. In some embodiments, the RFM further comprises a thermal heating cavity. In some embodiments, the thermal heating cavity is replaced by a microwave cavity. In some embodiments, the v-vials are 5-mL v-vials.

The RFM can be controlled by a National Instruments Compact Fieldpoint source module linked to a laptop computer running Labview Real-Time software source. The software used to control the radiofluorination module is built on the National Instruments LabVIEW professional and LabVIEW Real-Time platform. Exemplary configurations of the automated RFM and controlling software are depicted in Ravert et al. (Ravert, et al., 2014) and also described in Ravert et al. (Ravert et al., 2015) and such configurations are herein incorporated by reference in their entirety. In some embodiments, the hardware-software system allows full automation including steps from collection of the [$^{18}$F]-fluoride to the injection of the reaction mixture onto the semi-preparative HPLC. In some embodiments, a RFM can be configured for partial automation.

In some embodiments, [$^{18}$F]DCFPyL is synthesized using a ELIXYS automated radiochemistry synthesizer (Sofie Biosciences, Inc., Culver City, Calif.) (Lazarie et al., 2014). In some embodiments, only one of the three reactors of ELIXYS is used to synthesize [$^{18}$F]DCFPyL.

In general, components (e.g., valves or tubing) or surfaces of a synthesis module that are in contact or exposed to reactant(s), reaction intermediate(s), or product(s) should be made of or coated with inert materials and/or materials that are not reactive to, e.g., acids or bases and/or materials that minimize surface absorption of any reactant(s), reaction intermediate(s), or product(s) during radiosynthesis. In some embodiments, some or all of the components (e.g., valves or tubing) and/or surfaces of a synthesis module are free of fluorine in order to minimize any fluorine contamination in radiosynthesis. As used herein, the term "free of fluorine" refers to no more than 0.01% (including, e.g., no more than 0.005%, no more than 0.001%, no more than 0.0001%, or 0%) fluorine atoms or fluoride ions. In one embodiment, some or all of the components (e.g., valves or tubing) and/or surfaces of a synthesis module do not comprise fluoropolymer such as polytetrafluoroethylene.

In some embodiments, designs of fluid pathways that minimize transfer losses and transfer times from upright-positioned, small volume vessels are used.

Synthesis of DCFPyL Precursor, [$^{18}$F]Fluoride, and [$^{18}$F] Fluoride Standards In some embodiments, DCFPyL precursors can be synthesized by acylation reaction of compound A having structure (II) with compound B having structure (III) or a salt thereof:

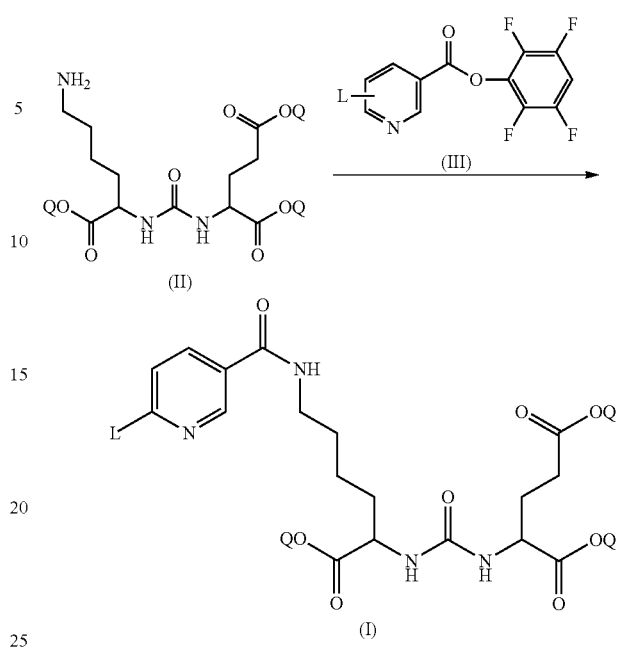

wherein Q in compound A having structure (II) is a protecting group of an ester moiety that is removable by treatment of phosphoric acid as defined above; and wherein L in compound B having structure (III) or a salt thereof is a leaving group as defined above.

In some embodiments, compound A having structure (II) is:

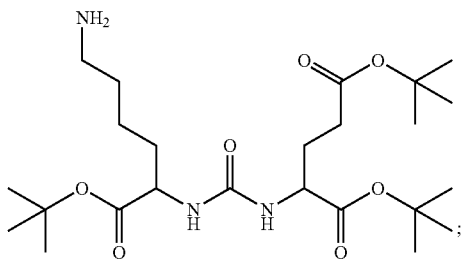

wherein Q is a tert-butyl group.

In some embodiments, compound B having structure (III) is:

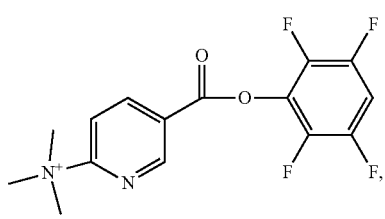 [SMILES: C[N+](C)(C)c1ccc(C(=O)Oc2c(F)c(F)cc(F)c2F)cn1]

with a counterion as defined above, and is preferably trifluoromethanesulphonate.

In some embodiments, a DCFPyL precursor (3, 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoromethanesulfonate) can be synthesized as depicted in FIG. 1 from the coupling of triflate salt of trimethylammonium nicotinic ester (2) and uriedo compound (1). Compound (1) in dichloromethane is mixed with triethylamine (TEA) and compound (2). After incubation at room temperature, the product can be dried, and a semi-solid is formed in acetonitrile and dimethyl ether. In some embodiments, vacuum can be applied for drying. The DCFPyL precursor can be purified using a C-18 column (e.g., a C-18 Sep-Pak Vac). The counterion of the DCFPyL precursor can be exchanged during purification. Thus, in some embodiments, the purified DCFPyL precursor is 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoromethanesulfonate. In some embodiments, the purified DCFPyL precursor is 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoroacetate. In some embodiments, the fractions can be lyophilized to form a white solid.

In some embodiments, [$^{18}$F]Fluoride can be produced by loading Oxygen-18 enriched water into a niobium body, high yield [$^{18}$F]fluoride target of a General Electric Medical Systems (GEMS, Uppsala, Sweden) PETtrace cyclotron, and irradiating the target with a proton beam.

Methods for the synthesis of ((2S)-2-[[(1S)-1-carboxy-5-[(6-fluoranylpyridine-3-carbonyl)-amino]-pentyl]-carbamoylamino]pentanedioic acid, the DCFPyL standard, ((2S)-2-[[(1S)-1-t-butylcarboxylate-5-[(6-fluoranylpyridine-3-carbonyl)-amino]-pentyl]-carbamoyl-amino]-di-t-butyl pentanedioate, the fluorinated protected intermediate standard, the formate salt 2-[3-[1-t-butylcarboxylate-(5-aminopentyl)]-uriedo]-di-t-butyl pentandioate (1) and N,N,N-trimethyl-5-((2,3,5,6-tetrafluorophenoxy)carbonyl)-pyridin-2-aminium trifluoromethanesulfonate (2) are provided herein. Examples of methods have been described (Chen, et al., 2011; Banerjee, et al., 2008; Olberg, et al., 2010), and the description of such methods are incorporated herein by reference in their entirety.

Radiofluorination, Deprotection and Purification

Methods for radiofluorinating a precursor as provided herein provided. In one embodiment, the method comprises:
(i) trapping [$^{18}$F]fluoride ion in a cartridge;
(ii) eluting the cartridge with a solution of tetrabutylammonium base salt (e.g., tetrabutylammonium hydrogen carbonate (TBABC)) to release the [$^{18}$F]fluoride ion trapped in the cartridge;
(iii) drying the eluate comprising the [$^{18}$F]fluoride ion;
(iv) adding a solution of DCFPyL precursor in an organic solvent or an aprotic solvent (e.g., acetonitrile) to the dried [$^{18}$F]fluoride ion; and
(v) heating the combined solution of step (iv).

In some embodiments, the cartridge can be rinsed with an organic solvent, such as acetonitrile after elution.

In some embodiments, all the chemicals and components are first loaded into the RFM or ELIXYS synthesis cassette. Then, [$^{18}$F]fluoride ions are delivered to an anion exchange cartridge, such as a Chromafix 30-PS-HCO3 Solid Phase Extraction (SPE) cartridge (ABX GmbH, Radeberg, Germany), which in some embodiments, is preconditioned by washing with high purity water. High purity water is commercially available, e.g., from Fluka. In some embodiments, high purity water can have an electrical conductivity of ~$10^{-8}$ S/cm (e.g., $5.5 \times 10^{-8}$ S/cm) (or approximately 10 MΩ·cm, e.g., 18 MΩ·cm in the reciprocal terms of electrical resistivity) at 25° C. In some embodiments, high purity water is sterile. In some embodiments, the volume of water used for preconditioning is 0.5-2 mL (e.g., 1 mL). In some embodiments, [$^{18}$O]Water is collected for recycling. In some embodiments, the resin cartridge with trapped [$^{18}$F]fluoride ions is then eluted with a solution of tetrabutylammonium hydrogen carbonate (TBABC). In some embodiments, between about 500 to about 700 μL (e.g., 600 μL) TBABC is used for elution when an RFM as described above is used. In some embodiments, between about 200 to about 400 μL (e.g., 300 μL) TBABC is used for elution when an ELIXYS system as described above is used. In some embodiments, other bases (e.g., potassium bicarbonate or potassium acetate with Kryptofix® 2.2.2) can be used. In some embodiments, the vials into which eluent is collected are cleaned with dilute nitric acid, washed with high purity water (e.g., HPLC water) and dried at 80° C. overnight.

In some embodiments, the solution comprising [$^{18}$F] fluoride ion eluted from the cartridge is dried at between about 80° C. to about 150° C. (e.g., 110° C.) with controlled nitrogen flow in a standard thermal heating block after rinsing the cartridge with acetonitrile. In some embodiments, a nitrogen flow between about 250 to about 400 mL/ml (e.g., 325 mL/min) for between about 50 seconds to about 300 seconds (e.g., 150 seconds) is used. In some embodiments, the solution comprising [$^{18}$F]fluoride ion eluted from the cartridge is dried azeotropically through one or more consecutive addition and removal of anhydrous acetonitrile. For example, in some embodiments, one or more (e.g., two, three or four) additions of acetonitrile are heated for between about 50 seconds to about 300 seconds each for further drying. For example, two separate additions of acetonitrile (250 μL each) can be heated for 150 seconds and 180 seconds, respectively, or 90 seconds and 105 seconds, respectively. In some embodiments, the acetonitrile can be heated under vacuum and nitrogen flow. In some embodiments, the vial is cooled using compressed air to a temperature of 40° C.-60° C. (e.g., 45° C. or 50° C.). In some embodiments, an air flow of 5-10 liters per min (e.g., 6 liters per min) is used.

A solution of the DCFPyL precursor (e.g., 3 in FIG. 5) in acetonitrile can then be added to the reaction vial containing the dried [$^{18}$F]fluoride ion. In some embodiments, the solution is heated between about 30° C. to about 70° C. (e.g., 45 or 50° C.) for between about 2 min to about 10 min (e.g., 5 min. or 6 min). In some embodiments, the solution is microwave irradiated at between about 40 W to about 60 W (e.g., 40 W, 50 W. or 60 W) for between about 20 seconds to about 200 seconds (e.g., 20, 30, 60, 100, 150 or 200 seconds).

For the deprotection step, between about 300 to about 400 μL (e.g., 350 μL) phosphoric acid (60-90%, e.g., 75% or 85%) or an acid with a pKa of 1.8 to 2.5 (e.g., 1.8, 1.9, 2.0, 2.1, 2.12, 2.2, 2.3, 2.4, 2.5) is added, e.g., without cooling the reaction mixture. In some embodiments, the vial is maintained at between about 30° C. to about 55° C. (e.g., 45° C.) for between about 2 min to about 10 min (e.g., 6 min). The reaction is then quenched and buffered to a pH of between about 2 to about 2.5. In some embodiments, quenching and buffering is achieved by addition of sodium hydroxide and sodium dihydrogen phosphate buffer. Exemplary concentrations and volumes of buffer reagents are as follows: (2M, 2 mL) and sodium dihydrogen phosphate buffer (10 mM, pH 2.1, 1 mL).

For purification of [$^{18}$F]DCFPyL, standard techniques known in the art can be applied. In some embodiments, the crude reaction mixture is injected onto a C18 column and eluted with a mixture of methanol and sodium dihydrogen phosphate. For example, the crude reaction mixture can be eluted with a mixture of 15:85 methanol: 0.01N sodium dihydrogen phosphate (pH 2.1). In some embodiments, [$^{18}$F]DCFPyL is collected in a reservoir of HPLC water. The collected fraction can be pushed by nitrogen through a C-18 Sep-pak Plus Long cartridge and rinsed to waste with HPLC water. In some embodiments, the radiotracer product is eluted with absolute ethanol followed by sterile saline through a 0.2-μm sterile filter. In some embodiments, the product is deposited into a sterile vial preloaded with sterile saline. In some embodiments, collection and/or elution is done in the presence of sodium ascorbate.

In some embodiments, the methods of synthesis of [$^{18}$F] DCFPyL produce large mCi quantities while conforming to all standard USP Chapter <823> acceptance testing criteria. In some embodiments, the radiosynthesis methods described herein has a yield of at least 20 mCi [$^{18}$F]DCFPyL, e.g., at least 30, at least 40, at least 50, at least 60, at least 70, at least 80, at least 90, at least 100, at least 150, at least 200, at least 300, at least 400, at least 500, at least 600 mCi [$^{18}$F] DCFPyL.

HPLC Analyses

For quality control HPLC analyses, various known analytical chromatography systems known in the art can be used. In some embodiments, the chemical and radiochemical properties of [$^{18}$F]DCFPyL can be determined using an Agilent 1260 Infinity system. An exemplary Agilent 1260 Infinity system configuration with a quaternary pump, HiP ALS autosampler, and DAD UV detector with a Max-Light flow cell set to 264 nm plus a Bioscan Flow-Count interface with a NaI radioactivity detector is described in Ravert et al. (*J. Label Compt. Radiopharm* 2014, 57: 695; *J. Label Compt. Radiopharm* 2015, 58: 180) and are herein incorporated by reference in their entirety. In some embodiments, an Agilent OpenLAB chromatography data system is used for collection and analysis of chromatographic data. One exemplary set of chromatographic conditions are as follows: an Atlantis T3 C18 5 μm 4.6×150 mm (Waters Corp., Milford, Mass.) column eluted with a mixture of 10:90 acetonitrile (MeCN):triethylamine (TEA)/phosphate buffer (pH 3.2) at a flow rate of 2 mL/min and UV set at 264 nm. In some embodiments, the following compounds can be used as standards for HPLC analysis: ((2S)-2-[[(1S)-1-carboxy-5-[(6-fluoranylpyridine-3-carbonyl)-amino]-pentyl]-carbamoylamino]pentanedioic acid, the DCFPyL standard, ((2S)-2-1[[(1S)-1-t-butylcarboxylate-5-[(6-fluoranylpyridine-3-carbonyl)-amino]-pentyl]-carbamoyl-amino]-di-t-butylpentanedioate, the fluorinated protected intermediate standard.

Compositions

Provided herein are compositions of the resultant products of any one of the methods provided herein. Such compositions can be used alone or in combination with other components or compounds as appropriate for their intended use.

In some embodiments, the [$^{18}$F]DCFPyL can have an average specific activity of at least 10 Ci/μmole, including, e.g., at least 20, at least 30, at least 40, at least 50, at least 60, at least 70, at least 80, at least 90, at least 100, at least 110, at least 120, at least 130, at least 140, at least 150 Ci/μmole, or higher. In some embodiments, the [$^{18}$F] DCFPyL can have an average specific activity of between about 40 to about 150 Ci/μmole.

In some embodiments, the compositions described herein comprise acetonitrile at a concentration of no more than about 400 ppm, including, e.g., no more than 300 ppm, no more than 200 ppm, no more than 100 ppm, no more than 50 ppm, no more than 25 ppm, no more than 10 ppm, no more than 5 ppm, no more than 1 ppm, or lower. In some embodiments, the compositions described herein do not comprise acetonitrile.

In some embodiments, the compositions described herein comprise methanol at a concentration of no more than about 3,000 ppm, including, e.g., no more than 2,000 ppm, no more than 1,000 ppm, no more than 500 ppm, no more than 250 ppm, no more than 100 ppm, no more than 50 ppm, no more than 10 ppm, no more than 1 ppm, or lower. In some embodiments, the compositions described herein comprise methanol at a concentration of between about 0-50 ppm.

In some embodiments, the compositions described herein do not comprise one or more cryptands, e.g., one or more Kryptofix® compounds.

In some embodiments, the compositions described herein do not comprise t-butanol.

In some embodiments, the compositions described herein do not comprise triethylamine.

In some embodiments, the compositions described herein do not comprise any of a cryptand, e.g., a Kryptofix® compound, t-butanol, and triethylamine.

In some embodiments, the compositions described herein have a radiochemical purity of [$^{18}$F]DCFPyL of at least 95% or higher, e.g., at least 96%, at least 97%, at least 98%, at least 99%, or up to 100%.

Apparatuses

Also, provided herein are synthesis modules that can be used to practice any one of the methods provided herein. Exemplary modules include the RFMs as described in the Examples, as well as the ELIXYS modified systems as provided herein. In preferred embodiments, the modules comprise the components of any one of the methods provided herein. In other preferred embodiments, the modules are those as described above as well as in the Examples.

Methods of Use

Also provided herein are methods of imaging one or more cells, organs or tissues comprising contacting the cells, organs or tissues or administering to a subject an effective amount of a compound as provided herein. In some embodiments, the one or more organs or tissues include prostate tissue, kidney tissue, brain tissue, vascular tissue or tumor tissue.

In one embodiment, the imaging method is suitable for imaging by targeting PSMA. In another embodiment, the imaging method is suitable for imaging of cancer, tumor or neoplasm. In a further embodiment, the cancer is selected from eye or ocular cancer, rectal cancer, colon cancer, cervical cancer, prostate cancer, breast cancer and bladder cancer, oral cancer, benign and malignant tumors, stomach cancer, liver cancer, pancreatic cancer, lung cancer, corpus uteri, ovary cancer, prostate cancer, testicular cancer, renal cancer, brain cancer (e.g., gliomas), throat cancer, skin melanoma, acute lymphocytic leukemia, acute myelogenous leukemia, Ewing's Sarcoma, Kaposi's Sarcoma, basal cell carcinoma and squamous cell carcinoma, small cell lung cancer, choriocarcinoma, rhabdomyosarcoma, angiosarcoma, hemangioendothelioma, Wilms Tumor, neuroblastoma, mouth/pharynx cancer, esophageal cancer, larynx cancer, lymphoma, neurofibromatosis, tuberous sclerosis, hemangiomas, and lymphangiogenesis.

The imaging methods provided herein are suitable for imaging any physiological process or feature in which PSMA is involved. In some embodiments, the imaging methods are suitable for identification of areas of tissues or targets which express high concentrations of PSMA. Exemplary applications include imaging glutamateric neurotransmission, presynaptic glutamatergic neurotransmission, malignant tumors or cancers that express PSMA, prostate cancer (including metastasized prostate cancer), and angiogenesis. Solid tumors express PSMA in the neovasculture. Therefore, methods and compositions provided herein can be used to image solid tumors including lung, renal cell, glioblastoma, pancreas, bladder, sarcoma, melanoma, breast, colon, germ cell, pheochromocytoma, esophageal and stomach. PSMA is frequently expressed in endothelial cells of capillary vessels in peritumoral and endotumoral areas of various malignancies such that the methods and compositions provided can be used for imaging such malignancies. Also, certain benign lesions and tissues including endometrium, schwannoma and Barrett's esophagus can be imaged according to the methods and compositions provided.

The methods and compositions for imaging angiogenesis provided are suitable for use in imaging a variety of diseases and disorders in which angiogenesis takes place. Illustrative, non-limiting, examples include tumors, collagen vascular disease, cancer, stroke, vascular malformations, and retinopathy. Methods and compositions of imaging angiogenesis provided are also suitable for use in diagnosis and observation of normal tissue development.

In certain embodiments of any one of the methods or compositions provided herein, the compositions of the radiolabeled compound have high specific activity, such as the levels of specific activity described herein.

In certain embodiments of any one of the methods or compositions provided herein, the radiolabeled compound is detected by positron emission tomography (PET) or position emission tomography/computed tomography (PET/CT). Images can be generated by virtue of differences in the spatial distribution of the imaging agents which accumulate at a site. The spatial distribution may be measured using any means suitable for the particular label, for example, a gamma camera, a PET apparatus, a PET/CT apparatus, and the like. The extent of accumulation of the imaging agent may be quantified using known methods for quantifying radioactive emissions.

In general, a detectably effective amount of a composition provided herein for imaging can be administered to a subject. In accordance with the invention, "a detectably effective amount" is defined as an amount sufficient to yield an acceptable image using equipment which is available for clinical use. A detectably effective amount of a composition provided herein may be administered in more than one injection. The detectably effective amount can vary according to factors such as the degree of susceptibility of the individual, the age, sex, and weight of the individual, idiosyncratic responses of the individual, and the dosimetry. Detectably effective amounts can also vary according to instrument and film-related factors. Optimization of such factors is well within the level of skill in the art. The amount of an imaging agent used for diagnostic purposes and the duration of the imaging study will depend upon the radionuclide used to label the agent, the body mass of the patient, the nature and severity of the condition being treated, the nature of therapeutic treatments which the patient has undergone, and on the idiosyncratic responses of the patient. Ultimately, the attending physician can decide the amount to administer to each individual patient and the duration of the imaging study.

In one embodiment of any one of the methods or compositions provided herein, the subject is a human, rat, mouse, cat, dog, horse, sheep, cow, monkey, avian, or amphibian. In another embodiment of any one of the methods or compositions provided herein, the cell is in vivo or in vitro. Typical subjects to which compounds of the invention may be administered are mammals, such as primates and humans. For veterinary applications, a wide variety of subjects include, e. g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals are suitable subjects including rodents (e.g. mice, rats, hamsters), rabbits, primates, and swine such as inbred pigs and the like. Additionally, for in vitro applications, such as in vitro diagnostic and research applications, body fluids and cell samples of any of the above subjects are suitable for use, such as human, blood, urine or tissue samples.

Other embodiments of the invention provide methods and compositions of treating tumors comprising administering to a subject a therapeutically effective amount of a composition provided herein, preferably in a therapeutically effective amount. In certain embodiments, the tumor cells may express PSMA, such as prostate tumor cells or metastasized prostate tumor cells. In other embodiments, a tumor may be treated by targeting adjacent or nearby cells which express PSMA. For example, vascular cells undergoing angiogenesis associated with a tumor may be targeted. The methods and compositions provided herein can be used to treat solid tumors including lung, renal cell, glioblastoma, pancreas, bladder, sarcoma, melanoma, breast, colon, germ cell, pheochromocytoma, esophageal and stomach (or any of the other cancers or tumors described herein or that are otherwise known to an ordinarily skilled artisan). Also, certain benign lesions and tissues including endometrium, schwannoma and Barrett's esophagus can be treated with the methods and compositions provided.

"Therapeutically effective amount" is that amount effective for a therapeutic purpose. Generally, in the context of a composition for administration to a subject refers to an amount of the composition that produces one or more desired responses in the subject. Therefore, in some embodiments, an amount effective is any amount of a composition provided herein that produces such a desired response. This amount can be for in vitro or in vivo purposes. For in vivo purposes, the amount can be one that a clinician would believe may have a clinical benefit for a subject. Such subjects include any one of those described herein. An amount that is therapeutically effective includes an amount of a composition provided herein that produces a desired therapeutic endpoint or a desired therapeutic result. The achievement of any of the foregoing can be monitored by routine methods.

Therapeutically effective amounts will depend on the particular subject being treated; the severity of a condition, disease or disorder; the individual patient parameters including age, physical condition, size and weight; the duration of the treatment; the nature of concurrent therapy (if any); the specific route of administration and like factors within the knowledge and expertise of the health practitioner. These factors are well known to those of ordinary skill in the art and can be addressed with no more than routine experimentation. It is generally preferred that a maximum dose be used, that is, the highest safe dose according to sound medical judgment. It will be understood by those of ordinary skill in the art, however, that a patient may insist upon a lower dose or tolerable dose for medical reasons, psychological reasons or for virtually any other reason.

Kits

Also provided are kits comprising any one of the compositions provided herein. In certain embodiments, the kit provides packaged pharmaceutical compositions comprising a pharmaceutically acceptable carrier and a composition of the invention. In other certain embodiments, the kit provides the compounds and reagents necessary to practice any one of the methods provided herein. In one embodiments of any one of the kits provided the kit further comprises indicia comprising at least one of: instructions for performing any one of the methods provided herein, for preparing any one of the compositions provided herein, or for the final radiolabeled compound as provided herein in a method of use, such as any one of the methods of use provided herein.

Kits comprising a DCFPyL precursor and a reagent for use in radiofluorination provided herein. In some embodiments, the kit comprises a DCFPyL precursor and phosphoric acid. In some embodiments, the kit comprises a DCFPyL precursor and tetrabutylammonium hydrogen carbonate, and optionally phosphoric acid. In some embodiments, the kit does not comprise one or more cryptands, e.g., Kryptofix® (for example, Kryptofix® 2.2.2). In some embodiments, the kit can further comprise [$^{18}$F]fluoride ions, e.g., [$^{18}$F]fluoride ions packaged in a radiation-resistant container.

In certain embodiments, the kit comprises any one of the compositions provided herein in combination with a pharmaceutically acceptable carrier. The composition of any one of the kits provided may be in solution or in lyophilized form. When in lyophilized form, the kit may optionally contain a sterile and physiologically acceptable reconstitution medium such as water, saline, buffered saline, and the like. In another embodiment, when in solution or in lyophilized form, the kit may optionally contain stabilizers such as NaCl, silicate, phosphate buffers, ascorbic acid, gentisic acid, and the like.

A "pharmaceutically acceptable carrier" refers to a biocompatible solution, having due regard to sterility, p[Eta], isotonicity, stability, and the like and can include any and all solvents, diluents (including sterile saline, Sodium Chloride Injection, Ringer's Injection, Dextrose Injection, Dextrose and Sodium Chloride Injection, Lactated Ringer's Injection and other aqueous buffer solutions), dispersion media, coatings, antibacterial and antifungal agents, isotonic agents, and the like. The pharmaceutically acceptable carrier may also contain stabilizers, preservatives, antioxidants, or other additives, which are well known to one of skill in the art, or other vehicle as known in the art.

As used herein, "pharmaceutically acceptable salts" refer to derivatives of the disclosed compounds wherein the parent compound is modified by making non-toxic acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, malefic, hydroxymaleic, phenylacetic, glutamic, benzoic, salicylic, mesylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, including 0, 1, 2, 3 and 4, and the like. The pharmaceutically acceptable salts of the present invention can be synthesized from a parent compound that contains a basic or acidic moiety by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are used, where practicable. Lists of additional suitable salts may be found, e.g., in Remington's Pharmaceutical Sciences, 17th ed., Mack Publishing Company, Easton, Pa., p. 1418 (1985). Pharmaceutically acceptable salts of the compounds provided herein can be used in any one of the methods or compositions provided.

As used in this specification and the appended claims, the singular forms "a," "an" and "the" include plural referents unless the content clearly dictates otherwise. Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Radiopharmacy Production Level Synthesis of [$^{18}$F]DCFPyL

The radiosynthesis of [$^{18}$F]DCFPyL on two distinct automated platforms with full regulatory compliant quality control specifications is described below. The radiotracer synthesis was performed on a custom-made radiofluorination module (RFM) and a Sofie Biosciences ELIXYS automated radiochemistry synthesizer. The RFM synthesis was accomplished in an average of 66 min from end-of-bombardment (EOB) with an average specific activity at end-of-synthesis (EOS) of 4.4 TBq/µmole (120 Ci/µmole) and an average radiochemical yield of 30.9% at EOS. The ELIXYS synthesis was completed in an average of 87 min with an average specific activity of 2.2 TBq/µmole (59.3 Ci/µmole) and an average radiochemical yield of 19% at EOS. Both synthesis modules produced large mCi quantities of [$^{18}$F]DCFPyL while conforming to all standard USP Chapter <823> acceptance testing criteria.

Under this example an improved synthesis of [$^{18}$F]DCFPyL from a single precursor with an automated synthesis performed both on an in-house custom-build synthesis module and a commercial radiochemistry module involved a single reactor, five operational steps, 65 min. to 87 min of synthesis time and resulted in an increased radiochemical yield. Using the methods provided herein, a radiopharmacy production level synthesis can be achieved.

Experimental Methodology

All chemicals and solvents were ACS or HPLC purity and were purchased through Sigma-Aldrich Chemical Company (St. Louis, Mo.) or Fisher Scientific (Waltham, Mass.) except where noted. The synthesis of ((2S)-2-[[(1S)-1-carboxy-5-[(6-fluoranylpyridine-3-carbonyl)-amino]-pentyl]-carbamoylamino]pentanedioic acid, the DCFPyL standard, ((2S)-2-[[(1S)-1-t-butylcarboxylate-5-[(6-fluoranylpyridine-3-carbonyl)-amino]-pentyl]-carbamoyl-amino]-di-t-butyl pentanedioate, the fluorinated protected intermediate standard, the formate salt 2-[3-[1-t-butylcarboxylate-(5-aminopentyl)]-uriedo]-di-t-butyl pentandioate (1) and N,N,N-trimethyl-5-((2,3,5,6-tetrafluorophenoxy)carbonyl)-pyridin-2-aminium trifluoromethanesulfonate (2) were synthesized as described (Chen, et al., 2011; Banerjee, et al., 2008; Olberg, et al., 2010). The descriptions of such synthesis methods, unless otherwise provided, are incorporated herein by reference in its entirety.

The custom-made radiofluorination module (RFM) was constructed and controlled in a similar fashion to a microwave radiosynthesis module (Ravert, et al., 2014), the description of which module is incorporated herein by reference in its entirety. However, a thermal heating cavity was substituted for a microwave cavity. The ELIXYS (Sofie Biosciences, Inc., Culver City, Calif.) module is a commercially available automated multireactor radiosynthesizer (Lazari, et al., 2014).

For routine quality control (QC) HPLC analyses, the chemical and radiochemical identities of [$^{18}$F]DCFPyL were determined using an Agilent 1260 Infinity System (Santa Clara, Calif.) incorporating a quaternary pump, HiP ALS autosampler, and DAD UV detector with a Max-Light flow cell set to 264 nm plus a Bioscan Flow-Count interface with a NaI radioactivity detector (Eckert & Ziegler, Berlin, Germany). Chromatographic data were acquired and analyzed on an Agilent OpenLAB chromatography data system (Rev. A.04.05). The following chromatographic conditions were used: an Atlantis T3 C18 5 µm 4.6×150 mm (Waters Corp., Milford, Mass.) column eluted with a mixture of 10:90 acetonitrile (MeCN):triethylamine (TEA)/phosphate buffer (pH 3.2) at a flow rate of 2 mL/min and UV set at 264 nm.

To examine the possibility of residual lipophilic starting materials, gradient HPLC analysis was performed using the same Agilent HPLC system and a Waters Corp. Atlantis dC18 5 µm 2.1×100 mm column initially equilibrated with solvent A (10:90 MeCN:TEA/phosphate buffer pH 3.2) at a flow rate of 1 mL/min. Solvent A (100%) was flowed from time of injection until 2.5 min when Solvent B (100% MeCN) linearly increased from 0 to 85% until the end of the chromatogram at 10 min.

Analyses of residual solvent levels in [$^{18}$F]DCFPyL batches were conducted using an Agilent 7890A gas chromatograph, Agilent OpenLAB chromatography data system for data acquisition and analysis, and a WAX (Polyethyleneglycol phase: USP G16, G20) 30 meters, 0.25 mm ID, 0.25-µm film column.

Synthesis of 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoromethanesulfonate (3)

1 (0.303 g, 0.57 mmole) was dissolved in 6 mL dichloromethane. To it was added 0.158 mL TEA and 2 (0.272 g, 0.57 mmole). The reaction mixture was stirred at room temperature for 1 hour. The solvent was then removed under a stream of $N_2$, followed by drying under vacuum. The mixture was dissolved in acetonitrile and diethyl ether added with stirring. The mixture was kept at room temperature for 30 min and a semi-solid was formed. The ether layer was removed and the semi-solid re-dissolved in acetonitrile. Diethyl ether was added with stirring to produce a semisolid. The mixture was kept at room temperature for 30 min, and the ether layer was removed. The semi-solid was dried under vacuum and purified on C-18 Sep-Pak Vac 35 cc (Waters Corp.) using acetonitrile/water (1:9 to 5:5 (v:v)). Fractions were collected and lyophilized to give white solid (0.322 g, 71%). 1H-NMR (500 MHz, MeOD) δ 9.04 (d, J=2.3 Hz, 1H), 8.54 (dd, J1=2.3 Hz, J2=8.7 Hz, 1H), 8.10 (d, J=8.7 Hz, 1H), 4.17 (m, 2H), 3.68 (s, 9H), 3.43 (m, 2H), 2.32 (m, 2H), 2.03 (m, 1H), 1.80 (m, 2H), 1.67 (m, 3H), 1.45-1.50 (m, 29H). 13C-NMR (500 MHz, MeOD) δ 174.0, 173.9, 173.6, 166.0, 160.1, 159.7, 149.5, 141.4, 134.3, 121.9 (q, J=317.9 Hz), 115.8, 83.0, 82.8, 81.9, 56.0, 54.9, 54.3, 41.1, 33.5, 32.6, 29.9, 29.1, 28.5, 28.4, 24.2. Elemental analysis: calcd for $C_{34}H_{56}F_3N_5O_{11}S$; C, 51.05; H, 7.06; N, 8.76; found C, 50.58; H, 6.95; N, 8.49. HR-MS calcd for $C_{33}H_{56}N_5O_8+$: 650.4123, found, 650.4138 [M]+.

Production of [$^{18}$F]Fluoride

Oxygen-18 enriched water (98%, Huayi Isotopes, Jiangsu, China, approx. 2 mL) was loaded into a niobium body, high yield [$^{18}$F]fluoride target of a General Electric Medical Systems (GEMS, Uppsala, Sweden) PETtrace cyclotron. The target was irradiated with a proton beam of 55 μA for 30 min to produce approx. 61 GBq (1.65 Ci) of aqueous [$^{18}$F]fluoride ions by the $^{18}$O(p,n)$^{18}$F nuclear reaction.

Radiosynthesis of [$^{18}$F]DCFPyL using the Radiofluorination Module (RFM)

After all chemicals and components were loaded into the RFM, [$^{18}$F]fluoride ion was delivered to a Chromafix 30-PS-HCO$_3$ SPE cartridge (ABX GmbH, Radeberg, Germany) earlier preconditioned by washing with 1 mL high purity water (Fluka). [$^{18}$O]Water was collected for recycling. Under RFM computer control (National Instruments LabVIEW, Austin, Tex.), the resin cartridge was eluted with a solution of tetrabutylammonium hydrogen carbonate (TBABC) (600 μL, 0.075M, ABX GmbH, Germany) into a 5 mL reaction vial sealed with a multiport cap; the vials were cleaned with dilute nitric acid, washed with HPLC water and dried at 80° C. overnight prior to the synthesis. After rinsing the cartridge with MeCN (250 μL), the solution was dried at 110° C. with controlled nitrogen flow (325 mL/min) for 150 seconds in a standard thermal heating block. To further dry the [$^{18}$F]fluoride ion, two separate additions of MeCN (250 μL each) were heated for 150 and 180 seconds, respectively.

The vial was cooled using compressed air (flow approx. 6 liters per min) to a temperature of 50° C. A solution of the DCFPyL precursor (3) (5 mg, 6.25 μmoles) in MeCN (500 μL) was added to the reaction vial containing the dried [$^{18}$F]fluoride ion. The solution was heated at 50° C. for 6 min. This was followed without cooling by the addition of phosphoric acid (85%, 350 μL). The vial was maintained at 45° C. for an additional 6 min. A mixture of sodium hydroxide (2M, 2 mL) and sodium dihydrogen phosphate buffer (10 mM, pH 2.1, 1 mL) was added to quench the reaction and buffer the reaction mixture to a pH of 2-2.5.

The crude reaction mixture was remotely injected onto a Phenomenex Gemini C18 5 μm 10×150 mm column (Torrance, Calif.) eluted with a mixture of 15:85 methanol (MeOH): 0.01M sodium dihydrogen phosphate (pH 2.1) at flow rate of 10 mL/min. [$^{18}$F]DCFPyL (RT=18 min, k'=15.4) was collected in a reservoir of HPLC water (70 mL). The collected fraction was pushed by nitrogen through a C-18 Sep-Pak Plus Long cartridge (Waters Corp.) and the cartridge was rinsed to waste with HPLC water (10 mL). The radiotracer product was eluted from the cartridge with absolute ethanol (1 mL) followed by sterile saline (10 mL) through a 0.2 μm sterile Millipore FG filter (25 mm; Merck KGaA, Darmstadt, Germany) into a sterile product vial preloaded with sterile saline (4 mL).

Radiosynthesis of [$^{18}$F]DCFPyL using ELIXYS

After all chemicals and components were loaded onto the ELIXYS synthesis cassette, the [$^{18}$F]fluoride ion was delivered to a 5 mL V-vial in a dose calibrator. The automated ELIXYS synthesis sequence was started. The [$^{18}$F]fluoride ion was pushed with nitrogen through a Chromafix 30-PS-HCO$_3$ SPE cartridge (ABX GmbH, Germany) previously preconditioned by washing with 1 mL high purity water (Fluka). [$^{18}$O]Water was collected for recycling. The resin cartridge was eluted with a solution of TBABC (300 μL, 0.075M, ABX GmbH, Germany) into the 5 mL reactor V-vial with glass stir bar in the ELIXYS reactor. After rinsing the cartridge with MeCN (600 μL), the solution was dried at 110° C. under vacuum and nitrogen flow for 270 seconds with stirring. Two separate additions of MeCN (600 μL) were heated under vacuum and nitrogen flow for 90 and 105 seconds, respectively.

The vial was cooled to a temperature of 45° C. A solution of the DCFPyL precursor (3) (5 mg, 6.25 μmoles) in MeCN (500 μL) was added to the reaction vessel containing the dried [$^{18}$F]fluoride. The solution was heated with stirring at 50° C. for 6 min. Phosphoric acid (85%, 350 μL) was added to the reaction vial. The reaction vial continued to be heated with stirring for an additional 6 min at 45° C. A mixture of 2 mL of sodium hydroxide (2M, 2 mL) and sodium dihydrogen phosphate (10 mM, pH 2.1, 1 mL) in 2 equal volume aliquots was added with stirring to quench the reaction and buffer the reaction mixture to a pH of 2-2.5.

The purification and formulation of the [$^{18}$F]DCFPyL was the same as described for the RFM radiosynthesis above.

Quality Control Procedures, Visual Inspection

Using remote handling equipment and appropriate radiation shielding (leaded glass), the vial containing the [$^{18}$F]DCFPyL product was visually inspected under bright light. The product met this acceptance specification if it was clear and colorless with no evidence of foreign matter.

Radiochemical Identity

A reference standard solution was injected on the analytical HPLC to establish the suitability of the system conditions (confirming a match to a standard curve examining retention time and mass). To determine the radiochemical identity, an aliquot (50 μL) of the final injection matrix of [$^{18}$F]DCFPyL was mixed with an aliquot of the reference standard solution. The product met this acceptance specification if the retention time of the reference material, as determined by UV detector was consistent with the retention time of the [$^{18}$F]DCFPyL, as determined by radiation detector, with appropriate correction for the offset between the two detector systems.

Radiochemical Purity

Using the same HPLC system described for the radiochemical identity test, an appropriate volume (50 μL) of [$^{18}$F]DCFPyL was injected at a quantity injected that avoids uncorrected dead-time loss (for main peak) in the radioactive detection system. The percent radiochemical purity of [$^{18}$F]DCFPyL was determined by dividing the radioactivity associated with the [$^{18}$F]DCFPyL peak by total activity assayed in the chromatogram multiplied by 100. The product met this acceptance specification if the radiochemical purity was greater than or equal to 95%. A sample QC chromatogram is shown in FIG. 7 (DCFPyL—RT=7.6 min., k'=8.7).

Specific Activity

The specific activity of [$^{18}$F]DCFPyL was calculated by dividing the assayed radioactivity of a calibrated aliquot of [$^{18}$F]DCFPyL (mCi/mL at end-of-synthesis) by the mass concentration of carrier DCFPyL measured by HPLC-UV (μmole of DCFPyL per mL) as interpreted from the standard mass calibration curve. The product met this acceptance specification if the specific activity was greater than or equal to 1000 mCi/μmole.

Chemical Purity

At high specific activity, the use of simple UV peak ratios as an indicator of chemical purity is inadequate as masses are typically diminishingly small. For a successful synthesis of [$^{18}$F]DCFPyL, not less than 99.5% of the starting precursor must be removed during the synthesis; thus, there may be not more than 0.5% of the precursor or its by-products remaining in the final product matrix. All other UV absorbing HPLC components that are not attributed to the matrix must also be less than the same permitted residual precursor concentration. Using the same HPLC system described for the radiochemical identity test, the carrier mass of [$^{18}$F]DCFPyL was determined. After the initial HPLC column void volume, all other UV peaks were summed and attributed to by-products. The product met this acceptance specification if the mass concentration of these by-products were less than or equal to 1.5 μg/mL.

Residual Solvent Analysis

An aliquot of a standard solution of 25 mL of HPLC water to which was added 1675 μL of absolute ethanol (6.7%), 12.7 μL of acetonitrile (400 ppm) and 94.7 μL of methanol (3000 ppm) was analyzed to determine system suitability. An aliquot of the final [$^{18}$F]DCFPyL product matrix was injected and the levels of residual solvent calculated by comparison to standards as if from a single-point curve. The product met this acceptance specification if the level of acetonitrile was less than or equal to 400 ppm, the level of methanol was less than or equal to 3000 ppm, and the ethanol level was less than or equal to 10% (Intl. Conf. on Harmonisation of Tech. Requirements for Registration of Pharm. for Human Use, 1997).

pH

A drop of the [$^{18}$F]DCFPyL final product matrix was applied to pH indicator paper (ColorPhast-Indicator strip—pH 2-9; sensitivity of 0.3 to 0.5 units, EMD Chemicals Inc., Gibbstown, N.J.). The strip color was matched to an indicator chart. The product met this acceptance specification if the pH was between 4.5 and 8.5.

Sterile Filter Integrity Test

The sterile microfilter from the [$^{18}$F]DCFPyL terminal filtration step was washed with 5 mL of absolute ethanol, left wetted, and attached to a calibrated pressure gauge (Millipore Corp.) and air pressure source. The distal end of the filter was placed in a liquid reservoir and the gas pressure was slowly increased. The product met the acceptance specification for the Millipore Millex FG filter integrity if a pressure of greater than or equal to 13 psi was reached without seeing a stream of bubbles.

Radionuclidic Identity

The radioactivity content (mCi) in an aliquot of the [$^{18}$F]DCFPyL final product matrix was determined in a Capintec CRC-15R Radioisotope Dose Calibrator (Ramsey, N.J.) at time (0 min; A) and again 15 min later (B). The half-life was calculated using the formula below. The product met this acceptance specification if the calculated half-life was between 105 and 115 min.

$$T_{1/2} = (4.495)/(\log A - \log B)$$

Radionuclidic Purity

Using a suitable gamma-ray spectrometer, an appropriate aliquot of the injection was assayed for a period of time sufficient to obtain a gamma spectrum. The resultant gamma spectrum was analyzed for the presence of identifiable photopeaks that were not characteristic of $^{18}$F emission. The product met this acceptance specification if not less than 99.5% of the total observed gamma emissions corresponded to 0.511 and 1.022 MeV for the radionuclidic purity.

Endotoxin Testing

Endotoxin levels in batches of the [$^{18}$F]DCFPyL final product matrix were analyzed using a Charles River Laboratories EndoSafe Portable Testing System (Endosafe PTS Reader, Integrated Software Version 7.10, Service Pack 2.0, and printer; Wilmington, Mass.). The product met this acceptance specification if the endotoxin level was less than or equal to 11 endotoxin units per mL.

Sterility Testing

In a laminar flow hood, samples of the [$^{18}$F]DCFPyL final product matrix (approx. 100 μL each) were added to fluid thioglycolate media and soybean casein digest medium (Becton, Dickinson and Company). The media were incubated at 32.5±2.5° C. and 22.5±2.5° C., respectively, and observed daily for any turbidity indicative of positive growth. The product met this acceptance specification if no growth was observed during the 14-day incubation period.

Retesting at Radiotracer Expiry

A subset of the above listed acceptance tests was performed 360 min after the end of the radiotracer synthesis to demonstrate the stability of the radiotracer product upon storage under ambient conditions.

Results and Discussion

Manual radiosynthesis of [$^{18}$F]DCFPyL (Chen, et al., 2011) was adapted for routine use on an automated, dual reactor synthesis platform (an old Nuclear Interface "Double FDG Synthesis Module"). As part of the original qualification of the radiotracer synthesis for human use, a moderate amount of the final radiotracer product (2.3 GBq; 62 mCi average) with a specific activity at end of synthesis of 192 GBq/μmole (5.2 Ci/μmole) was produced. Table 1 shows the original acceptance specifications and results for qualifying productions. Over time, the procedure produced a somewhat variable radiochemical yield of approx. 3% (not corrected for decay, based upon estimated average [$^{18}$F]fluoride target yields) with frequently lower on average specific activities at end of synthesis for over 110 radiochemical syntheses performed over a 2-year period of time.

Table 1. QC Acceptance Specifications: Comparison of Original Synthesis of [$^{18}$F]DCFPyL with New Synthesis on RFM and ELIXYS Modules. (All tests except yield, specific activity and filter integrity were repeated at 360-min expiry and agreed with testing results performed at EOS.)

| Acceptance Specifications in Original Application for First-in-Human Studies | | | | Revised Acceptance Specifications for this Synthesis (2016) | | | |
|---|---|---|---|---|---|---|---|
| Test | Specification | Average Original (n = 3) | Change in Revised Specification | Test | Specification | Average RFM (n = 3) | Average ELIXYS (n = 3) |
| Initial appearance | Clear, colorless solution, no visible particulate matter | Conforms | No change | Initial appearance | Clear, colorless solution, no visible particulate matter | Conforms | Conforms |
| Appearance. 240 min after EOS | Clear, colorless solution, no visible particulate matter | Conforms | Expiry extended to 360 min | Appearance, 360 min after EOS | Clear, colorless solution, no visible particulate matter | Conforms | Conforms |

| | Acceptance Specifications in Original Application for First-in-Human Studies | | | Revised Acceptance Specifications for this Synthesis (2016) | | | |
|---|---|---|---|---|---|---|---|
| Test | Specification | Average Original (n = 3) | Change in Revised Specification | Test | Specification | Average RFM (n = 3) | Average ELIXYS (n = 3) |
| Initial radiochemical purity, % | ≥95% | 100% | No change | Initial radiochemical purity, % | ≥95% | 99.9% | 100% |
| Expiry radiochemical purity, % | ≥95% | 100% | Expiry extended to 360 min | Expiry radiochemical purity, % | ≥95% | 100% | 100% |
| pH, initial | 4.5-8.5 | 5 | No change | pH, initial | 4.5-8.5 | 5 | 5 |
| pH, initial | 4.5-8.5 | 5 | No change | pH, expiry | 4.5-8.5 | 5 | 5 |
| Chemical purity | DCFPyL | 0.33 ± 0.06 µg/mL | No change | Chemical purity | DCFPyL | 0.14 ± 0.03 µg/ml | 0.19 ± 0.08 µg/ml |
| | All other impurities ≤1.5 µg/mL | 0.05 ± 0.05 µg/mL | | | All other impurities ≤1.5 µg/mL | 0.08 ± 0.08 µg/mL | 0.10 ± 0.09 µg/mL |
| Yield | ≥20 mCi [$^{18}$F]DCFPyL (referenced to assay recorded at end of filtration) | 62.4 ± 10.4 mCi | No change | Yield | ≥20 mCi [18F]DCFPyL (referenced to recorded at end of filtration) | 561.7 ± 91.3 mCi | 372.0 ± 199.1 mCi |
| Specific activity | ≥1000 mCi/µmol of [18F]DCFPyL (referenced to end of filtration) | 5210 ± 728 mCi/µmol | No change | Specific activity | ≥1000 mCi/µmol of [18F]DCFPyL (referenced to end of filtration) | 119 950 ± 9165 mCi/µmol | 59 335 ± 12 417 mCi/µmol |
| Residual solvent analysis | Acetonitrile ≤400 ppm | 0 ppm | Triethylamine and t-butanol no longer used; methanol added | Residual solvent analysis | Acetonitrile ≤400 ppm | 0 ppm | 0 ppm |
| | Triethylamine ≤400 ppm | 0 ppm | | | Methanol ≤3000 ppm | 17.7 ± 0.6 ppm | 19.6 ± 18.7 ppm |
| | t-Butanol ≤400 ppm | 0 ppm | | | | | |
| Radionuclidic identity | $t_{1/2}$ = 105-115 min | 110.6 ± 3.0 min | No change | Radionuclidic identity | $t_{1/2}$ = 105-115 min | 109.5 ± 2.2 min | 110.8 ± 2.0 min |
| Radionuclidic purity | 99.5% associated with $^{18}$F (0.511 and 1.022 MeV) | Conforms | No change | Radionuclidic purity | 99.5% associated with 18F (0.511 and 1.022 MeV) | Conforms | Conforms |

Prior methods resulted in variable yields and only low to moderate specific activities. Provided herein is an [$^{18}$F]DCFPyL synthesis method of higher radiochemical yield and increased specific activity while meeting or exceeding all previously established QC criteria. Alternative precursors for the radiotracer synthesis, alternative synthesis platforms (including developing an in-house custom made system), and modifying reaction and purification conditions were established to achieve a larger scale radiopharmacy-level production of the radiotracer.

A new precursor was synthesized. A successful chemical synthesis of the protected trimethylammonium precursor (3) (FIG. 1) allowed the radiotracer synthesis of [$^{18}$F]DCFPyL to evolve. The precursor, 5-(((S)-6-(tertbutoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoromethanesulfonate (3), was synthesized from the coupling of the triflate salt of the trimethylammonium nicotinic ester (2) and the ureido compound (1) in suitable yield.

Radiofluorination of the trimethylammonium precursor (3) at 50° C. produced a clean reaction profile in high yield with the TBABC base. While other bases (e.g., potassium bicarbonate or potassium acetate with Kryptofix® 2.2.2) were examined, these typically resulted in lower yields. Increasing the quantity of precursor used in the synthesis above 5 mg did not provide an increased radiofluorination yield. On the RFM, increasing the amount of TBABC from 11.25 to 22.5 to 45 µmoles increased the yield from 10 to 30%. Using gradient HPLC (conditions described in the experimental methods section), an 81% yield of the radiofluorinated protected intermediate was observed (FIG. 2, RT=8.9 min). Superimposed on the gradient HPLC is the UV trace of the trimethylammonium precursor and nonradioactive fluorinated protected intermediate (Chen, et al., 2011) as references (FIG. 3).

After radiofluorination, the deprotection of the ester moieties with a number of different acids was attempted resulting in low yields and by-product formation. Phosphoric acid (pKa1=2.12) was found to be sufficiently acidic to remove the butyl groups in a suitable yield (Li, et al., 2006) but not form major radiochemical by-products at 45° C. A gradient HPLC of the final crude deprotected product (RT=2.0 min) showed a good yield with no radiofluorinated protected intermediate or trimethylammonium precursor remaining in solution (FIG. 4).

Attention was turned to appropriate platforms for performing the synthesis under automation. The in-house, custom-made RFM (a thermal heating adaptation of the microwave synthesis module for making the α7-nicotinergic ligand, [$^{18}$F]ASEM at high specific activity (Ravert, et al., 2015)) was constructed. With some modifications, components (valves, tubings, etc.) that were free of fluorine in their manufacturing to minimize any fluorine contamination in the synthesis and the design of fluid pathways that minimize transfer losses and transfer times from upright-positioned, small volume reagent vessels resulted in the RFM, a simple computer controlled synthesis device (using National Instruments LabVIEW software). The software used to control the radiofluorination module is built on the National Instruments LabVIEW professional and LabVIEW Real-Time platform. The hardware-software interface is achieved using a National Instruments compactRio embedded controller. The National Instruments LabVIEW professional and LabVIEW Real-Time platform is the end users' interface with the National Instruments embedded controller. The end user modifies instrument subroutines from a library and custom designs and programs the radiofluorination module user interface to control and monitor the module performance.

The radiochemical synthesis was transferred to the Sofie Biosciences ELIXYS module. ELIXYS is a three reactor system that utilizes replaceable cassettes that provide its fluid pathways and allow the use of one or any combination of the three reactors and cassettes in a synthesis sequence (Lazari, et al., 2014). For this synthesis, only a single cassette and reactor were needed. The software has an interface that is simple and easily modified for method development or adaptation of existing syntheses. Although potential sources of fluorine contamination have not been rigorously eliminated on ELIXYS, [$^{18}$F]DCFPyL was obtained in suitable yield at high specific activity. To decrease drying time, less aqueous TBABC solution was utilized and this may have lowered somewhat the final yield. With the unique integration of robotics for reagent transfers and moveable reactors, ELIXYS synthesis times were longer than the RFM.

The final radiosynthesis scheme of [$^{18}$F]DCFPyL on the custom-made RFM and the Sofie ELIXYS radiosynthesis modules is outlined in FIG. 5. With the exception of the amount of TBABC in water that is added (600 µL for the RFM vs. 300 µL for the ELIXYS) and the split addition of reaction diluent solution for the ELIXYS prior to HPLC purification vs. the single larger volume addition for the RFM, the radiochemical syntheses are identical processes.

In both modules, the [$^{18}$F]fluoride ion was trapped on a Chromafix 30-PS-HCO3 cartridge, eluted from that cartridge with a solution of TBABC in water, and azeotropically dried with heating and additional acetonitrile. An acetonitrile solution of the DCFPyL trimethylammonium precursor (3) was added to the reaction vial and the vial was heated. Phosphoric acid was added to remove the t-butyl protecting groups with heating. The pH of the crude [$^{18}$F] DCFPyL solution was adjusted to 2-2.5 with the addition and thorough mixing of the sodium hydroxide and sodium dihydrogen phosphate buffer. Injection onto the semi-preparative HPLC column produced a typical chromatogram as displayed in FIG. 6. The [$^{18}$F]DCFPyL peak was collected in a water reservoir and an automated solid phase extraction (SPE) formulation was performed resulting in a final product solution of 1 mL ethanol and 14 mL normal saline.

The final sterile solution obtained from the RFM radiosynthesis contained an average of 20.8±3.4 GBq (562±91 mCi; n=3) of [$^{18}$F]DCFPyL with an average specific activity of 4.4±0.3 TBq/µmole (120±9.2 Ci/µmole EOS, not corrected for decay). The average EOS non-decay corrected yield was 30.9±3.0% in an average synthesis time of 66 min. The final sterile solution obtained from the ELIXYS radiosynthesis contained an average of 13.8±7.4 TBq (372±199 mCi; n=3) of [$^{18}$F]DCFPyL with an average specific activity of 2.2±0.5 TBq/µmole (59.3±12.4 Ci/µmole EOS, not corrected for decay). The average EOS non-decay corrected yield was 19.4±7.8% in an average synthesis time of 87 min. Both of these platforms vastly improved the mCi yield and specific activity compared to our original multistep synthesis of [$^{18}$F]DCFPyL that produced an average of 2.3 GBq (62 mCi) with an uncorrected specific activity at EOS of 193 GBq/µmole (5.2 Ci/µmole) in approx. 90 min.

Complete QC data, for both radiosynthesis modules, of the initial 3 verification runs of [$^{18}$F]DCFPyL produced using the methods disclosed herein are summarized in Table 1. These newly reported results meet or exceed all previously stated acceptance specifications. The only changes were the vastly improved amounts of [$^{18}$F]DCFPyL made with significantly improved radiotracer quality (as demonstrated by the large increases in the final specific activity of the radiotracer product). Two solvents previously used were no longer present in the synthesis and Kryptofix® 2.2.2 was no longer used and thus did not require a final acceptance limit and acceptance specification.

A typical QC chromatogram for chemical and radiochemical purity determinations and a co-injection ("spiked authentic") chromatogram for the purpose of chemical identity are shown in FIG. 7. Carrier mass determinations were performed from a calibration curve generated from 7 mass levels of nonradioactive DCFPyL (6-replicate injections per mass level) relating mass to UV absorbance prepared spanning 0.0046 and 0.2967 nmoles with an average goodness of fit ($R^2$) of 0.999985. The lower limit (0.0046 nmoles) was established as the limit of quantitation with a signal-to-noise ratio of 6:1. The limit of detection was determined to be approx. one-half that amount (0.0023 nmoles) (USP (1225)). A gradient HPLC of the final formulated solution of [$^{18}$F] DCFPyL showed no radiofluorinated protected intermediate or trimethylammonium precursor present (FIG. 8).

An adaption of the manual synthesis to an automated synthesis platform involved 10 operational steps (trapping fluoride, releasing and drying fluoride, reaction with first precursor, intermediate purification of first precursor, reaction with second precursor, evaporation of reaction solvent, deprotection of tbutyl protected radiofluorinated intermediate with trifluoroacetic acid, removing the acid, buffering for preparative chromatography, purification by HPLC, and formulation of final product). Synthesis with such adaptation used a module with two separate reactors. In the synthesis described herein there can be fewer operational steps in part due to the use of a single precursor and deprotection of the penultimate product without the need for solvent evaporation or removing acid prior to preparative HPLC purification. Without the inherent losses of radioactivity during solution transfers, evaporations, and intermediate purification, and the added benefit of shorter reaction times resulting in less radioactivity decay, the current synthesis shows a higher radiochemical yield at EOS compared to the other synthesis.

Finally, to illustrate the potential for large-scale (multi-Curie) production of [$^{18}$F]DCFPyL, a synthesis using the RFM module produced 83.6 Gbq (2.26 Ci) of [$^{18}$F]DCFPyL from 213 GBq (5.77 Ci) of starting [$^{18}$F]fluoride representing a 39.2% yield (EOS). The specific activity (EOS) was 4.7 TBq/µmole (127.3 Ci/µmole) with a radiochemical purity of 97.6%. At EOS, all other QC data were within the acceptance specifications set in Table 1. However, a reexamination of this large-scale radiotracer product at the established 6-hour expiry showed the product to be only 51.1% radiochemically pure. While the previous highest product yield validation run was 1.6 GBq/mL (44 mCi/mL) and was confirmed to meet all QC acceptance specifications at the 6-hour expiry, at 5.7 GBq/mL (153 mCi/mL), considerable radiotracer degradation was observed. A subsequent large-scale synthesis using the RFM module in which sodium ascorbate was added to the HPLC collection reservoir and the saline solution used for eluting the product from the Sep-Pak after ethanol elution produced 67.7 Gbq (1.83 Ci) of [$^{18}$F]DCFPyL from 222 GBq (6.0 Ci) of starting [$^{18}$F]fluoride representing a 30.5% yield (EOS). The specific activity (EOS) was 5.9 TBq/μmole (159.3 Ci/μmole) with a radiochemical purity of 99.7%. At EOS, all other QC data were within the acceptance specifications set in Table 1. The radiochemical purity of this 4.5 GBq/mL (122 mCi/mL) solution of [$^{18}$F]DCFPyL contained added sodium ascorbate at 3, 4, and 6 hours post EOS were 98.8%, 98.5%, and 98.2%, respectively.

Summary

A custom, high yield, ultra-high specific activity radiofluorination synthesis module used has been designed and constructed for the production of [$^{18}$F]radiotracers such as the PSMA inhibitor [$^{18}$F]DCFPYL. The specific activity of PET radiotracer is a critical quality control release criteria for mass-dependent receptor localization or pharmacologic toxicity concerns. At ultra-high specific activity, the radiotracer expiration time can be extended, allowing for more PET studies for a single produced batch of the radiotracer. The radiofluorination module allows for automated and semi-automation radiochemistry syntheses of radiotracers used for PET imaging. Currently there are more than 10 commercial radiochemistry synthesis modules available on the market today. What makes this chemistry module unique is the quality of the radiotracers that are produced using the module. The presently disclosed custom radiofluorination module has specific activities of 10-200 times greater than any of the commercial synthesis modules available on the market today.

The radiofluorination module can be used to product [$^{18}$F]radiotracers including but not limited to: [$^{18}$F]DCFPYL, [$^{18}$F]ASEM, [$^{18}$F]T807, and [$^{18}$F]AZAN.

[$^{18}$F]DCFPyL was prepared in moderate to high radiochemical yield at very high specific activity. Full regulatory acceptance specifications were described and met for each batch of radiotracer synthesized. This synthesis using either of these automated modules easily provides a sufficient amount of high quality [$^{18}$F]DCFPyL radiotracer product for up to 6 PET/CT scans (at 9 or 10 mCi per dose) a day injected and imaged one hour apart.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

B. Li, M. Berliner, R. Buzon, C. K. F. Chiu, S. T. Colgan, T. Kaneko, N. Keene, W. Kissel, K. R. Leeman, B. Marquez, R. Morris, L. Newell, S. Wunderwald, M. Witt, J. Weaver, Z. Zhang, Z. Zhang, J. Org. Chem, 2006, 71, 9045.

D. E. Olberg, J. M. Arukee, D. Grace, O. K. Hjelstuen, M. Solbakken, G. M. Kindberg, A. Cuthbertson, J Med Chem, 2010, 53, 1732.

H. T. Ravert, D. P. Holt, R. F. Dannals, A microwave radiosynthesis of the 4-[$^{18}$F]-fluorobenzyltriphenylphosphonium ion, J Label Compds Radiopharm, 2014, 57, 695.

H. T. Ravert, D. P. Holt, Y. Gao, A. G. Horti, R. F. Dannals, Microwave-assisted radiosynthesis of [$^{18}$F]ASEM, a radiolabeled α7-nicotinic acetylcholine receptor antagonist, J Label Compds Radiopharm, 2015, 58, 180.

K. Raisa, PET Radiochemistry Automation: State of the Art and Future Trends in 18F-nucleophilic Fluorination, Current Organic Chemistry, Volume 17, Number 19, October 2013, pp. 2097-2107(11).

International Conference on Harmonisation of Technical Requirements for Registration of Pharmaceuticals for Human Use. ICH Harmonised Tripartite Guideline Impurities: Guideline for Residual Solvents, 1997.

M. Dietlein, C. Kobe, G. Kuhnert, A. Stockter, T. Fischer, K. Schomacker, M. Schmidt, F. Dietlein, B. D. Zlatoposkly, P. Krapf, R. Richarz, S. Neubauer, A. Drzezga, B. Neumaier, Mol Imaging Biol, 2015, 17, 575.

M. Lazari, J. Collins, B. Shin, M. Farhoud, D. Yeh, B. Maraglia, F. T. Chin, D. A. Nathanson, M. Moore, R. M. van Dam, J Nucl Med Tech, 2014, 42, 1.

R. Seigel, J. Ma, Z. Zhou, A. Jemal, C A Cancer J Clin 2014, 64, 9.

R. C. Mease, C. L. Dusich, C. A. Foss, H. T. Ravert, R. F. Dannals, J. Seidel, A. Prideaux, J. J. Fox, G. Sgouros, A. P. Kozikowski, M. G. Pomper, Clin. Can. Res. 2008, 14, 3036.

S. R. Banerjee, C. A. Foss, M. Castanares, R. C. Mease, Y. Byun, J. J. Fox, J. Hilton, S. E. Lupold, A. P. Kozikowski, M. G. Pomper, J. Med. Chem, 2008, 51, 4504.

T. Maurer, M. Eiber, M. Schwaiger, J. E. Gschwend, Nature Rev./Urology 2016, 13, 226.

U.S. Pharmacopeia Chapter <823> Radiopharmaceuticals for Positron Emission Tomography—Compounding. USP 32-NF29, 2009.

USP (1225) "Validation of Compendial Methods".

V. Bouvet, M. Wuest, H. S. Jans, N. Janzen, A. R. Genady, J. F. Valliant, F. Benard, F. Wuest, Eur J Nucl Med Mol Imaging Research, 2016, 6, 40.

Y. Chen, M. Pullambhatia, C. A. Foss, Y. Byun, S. Nimmagadda, S. Senthamizchelvan, G. Sgouros, R. C. Mease, M. G. Pomper, Clin. Can. Res. 2011, 17, 7645.

Z. Szabo, E. Mena, S. P. Rowe, D. Plyku, R. Nidal, M. A. Eisenberger, E. S. Antonarakis, H. Fan, R. F. Dannals, Y. Chin, R. C. Mease, M. Vranesic, A. Bhatnagar, G. Sgouros, S. Y. Cho, M. G. Pomper, Mol Imaging Biol, 2015, 17, 565.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A method of synthesizing 2-(3-{1-carboxy-5-[(6-[$^{18}$F]fluoro-pyridine-3-carbonyl)-amino]-pentyl}-ureido)-pentanedioic acid [$^{18}$F]DCFPyL),

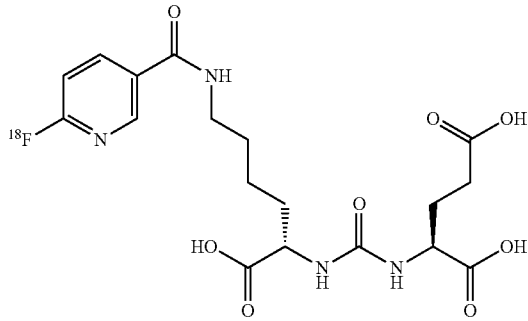 [SMILES: O=C(O)CC[C@H](NC(=O)N[C@@H](CCCCNC(=O)c1ccc([18F])nc1)C(=O)O)C(=O)O]

the method comprising:
(i) radiofluorinating a DCFPyL precursor comprising ester moiety protecting groups to form a radiofluorinated DCPFPyL precursor;
(ii) deprotecting the ester moiety protecting groups of the radiofluorinated DCPFPyL precursor of step (i) with phosphoric acid to form [$^{18}$F]DCFPyL in a reaction mixture; and (iii) purifying the [$^{18}$F]DCFPyL from the reaction mixture of step (ii) to provide [$^{18}$F]DCFPyL.

2. The method of claim 1, wherein the protecting groups are selected from the group consisting of benzyl, p-methoxybenzyl, tertiary butyl, methoxymethyl, methoxyethoxymethyl, methylthiomethyl, tetrahydropyranyl, tetrahydrofuranyl, benzyloxymethyl, trimethylsilyl, triethylsilyl, t-butyldimethylsilyl (TBDMS), and triphenylmethyl.

3. The method of claim 1, wherein step (i) and step (ii) are performed in one reactor.

4. The method of claim 1, wherein the synthesizing is automated by use of a radiofluorination module (RFM) comprising a heating block, two syringe pumps, a multi-port cap, and valved reagent addition vials.

5. The method of claim 4, wherein the RFM further comprises a thermal heating cavity.

6. The method of claim 4, wherein components of the RFM or the automated radiochemistry synthesizer are free of fluorine.

7. The method of claim 1, wherein the synthesizing is automated by use of an automated radiochemistry synthesizer.

8. The method of claim 1, wherein the DCFPyL precursor is 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium compound.

9. The method of claim 8, wherein the DCFPyL precursor is 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoromethanesulfonate.

10. The method of claim 8, wherein the DCFPyL precursor is 5-(((S)-6-(tert-butoxy)-5-(3-((S)-1,5-di-tert-butoxy-1,5-dioxopentan-2-yl)ureido)-6-oxohexyl)carbamoyl)-N,N,N-trimethylpyridin-2-aminium trifluoroacetate.

11. The method of claim 9, wherein the DCFPyL precursor is synthesized according to

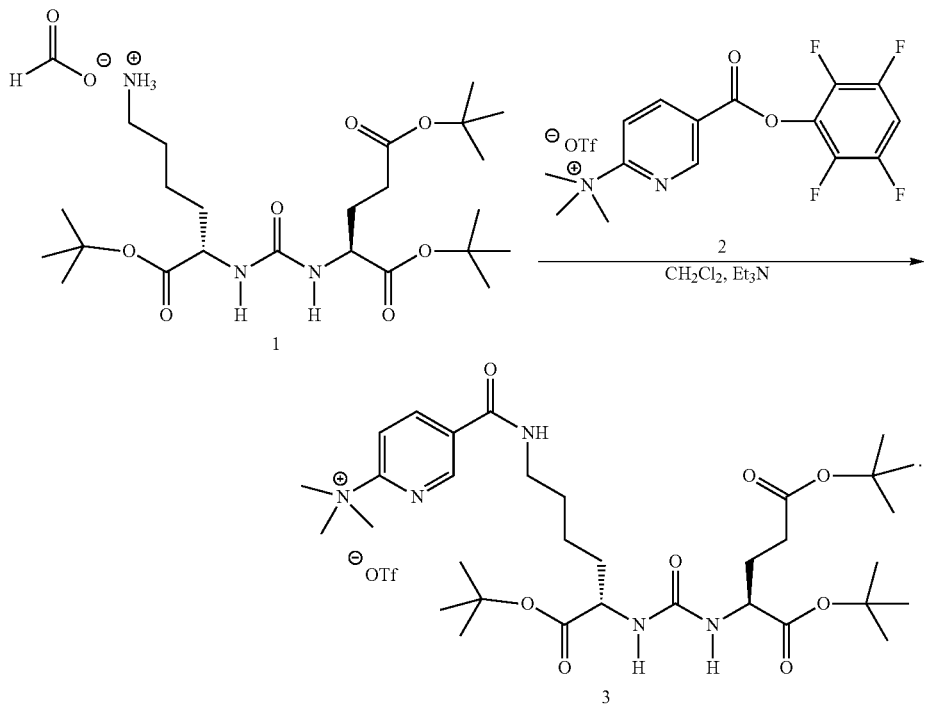

12. The method of claim 9, wherein the DCFPyL precursor is synthesized by a method comprising:
coupling of N,N,N-trimethyl-5-((2,3,5,6-tetrafluorophenoxy)carbonyl)-pyridin-2-aminium trifluoromethanesulfonate and 2-{3-[1-t-butylcarboxylate-(5-aminopentyl)]-ureido]-di-t-butyl pentandioate.

13. The method of claim 9, wherein the method further comprises synthesizing the DCFPyL precursor according to

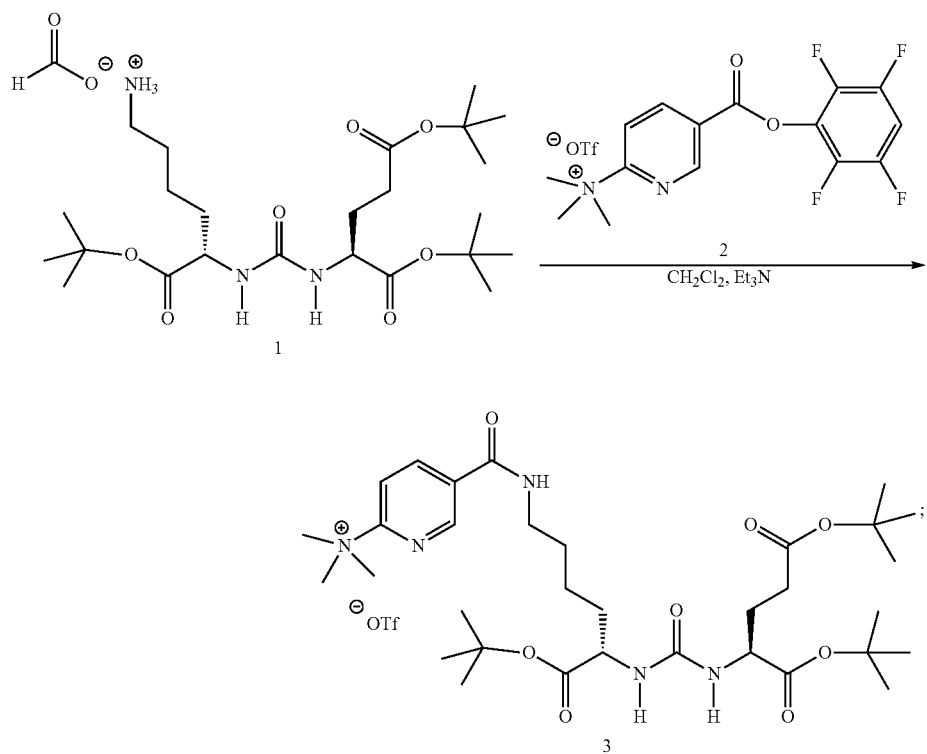
or by coupling of N,N,N-trimethyl-5-((2,3,5,6-tetrafluorophenoxy)carbonyl)-pyridin-2-aminium trifluoromethanesulfonate 2-[3-[1-t-butylcarboxylate-(5-aminopentyl)]-uriedo]-di-t-butyl pentandioate.
14. The method of claim 1, wherein the radiofluorinating a DCFPyL precursor is performed according to
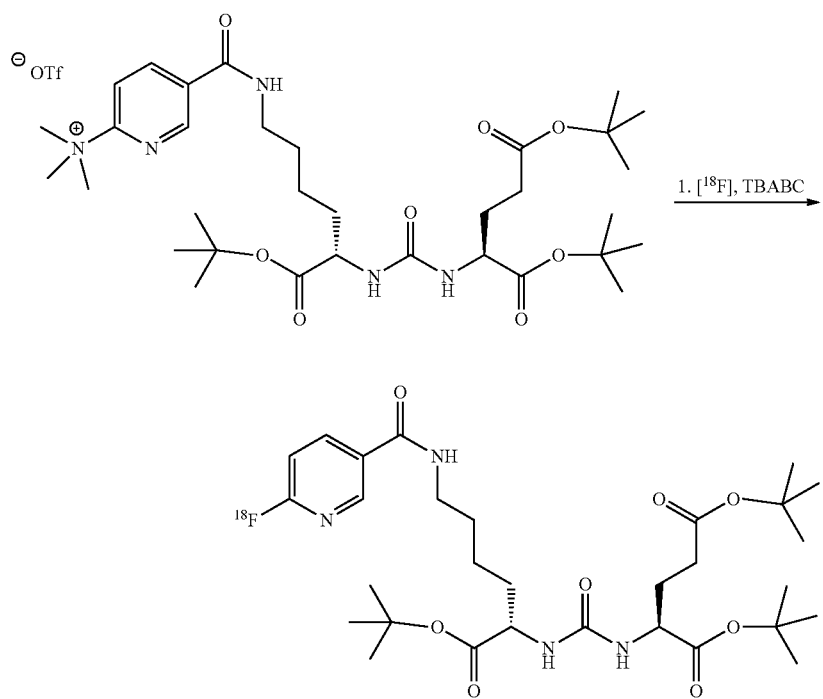

15. The method of claim 1, wherein the radiofluorinating a DCFPyL precursor comprises:
   (a) trapping [$^{18}$F]fluoride ion in a cartridge;
   (b) eluting the cartridge with a solution of tetrabutylammonium base salt to release the [$^{18}$F]fluoride ion trapped in the cartridge;
   (c) drying the eluate comprising the [$^{18}$F]fluoride ion to form dried [$^{18}$F]fluoride ion; and
   (d) adding a solution of (compound (3))

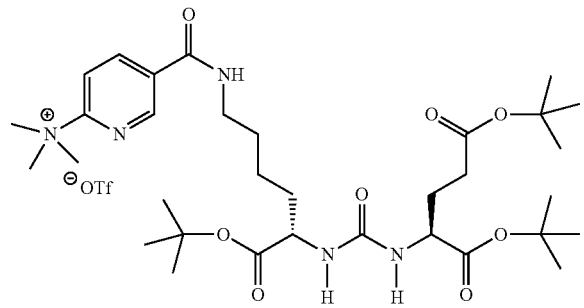

to the dried [$^{18}$F]fluoride ion.

16. A composition comprising [$^{18}$F]DCFPyL produced by the method of claim 1, wherein the [$^{18}$F]DCFPyL has a specific activity of at least 40 Ci/μmol.

17. A kit comprising the composition of claim 16.

18. A method of imaging comprising contacting cells, organs or tissues with a composition of claim 16.

19. A method of administering to a subject a composition of claim 16, and imaging the subject.

20. The composition of claim 16, wherein the composition has a specific activity of at least 60 Ci/mmol.

21. The composition of claim 20, wherein the composition has a specific activity of at least 100 Ci/mmol.

22. The composition of claim 21, wherein the composition has a specific activity of at least 120 Ci/mmol.

23. The composition of claim 22, wherein the composition has a specific activity of at least 150 Ci/mmol.

24. The method of claim 1, further comprising adjusting the pH of the reaction mixture of step (ii) after the deprotecting with phosphoric acid to a pH of between 2 to 2.5.

25. The method of claim 1, wherein the purifying is performed by liquid chromatography.

26. The method of claim 25, wherein the liquid chromatography involves at least one C18 column.

27. A method of radiofluorinating a DCFPyL precursor, which comprises:
   (i) trapping [$^{18}$F]fluoride ion in a cartridge;
   (ii) eluting the cartridge with a solution of tetrabutylammonium hydrogen carbonate (TBABC) to release the [$^{18}$F]fluoride ion trapped in the cartridge,
   (iii) drying the eluate comprising the [$^{18}$F]fluoride ion from step (ii);
   (iv) adding a solution of (compound (3))

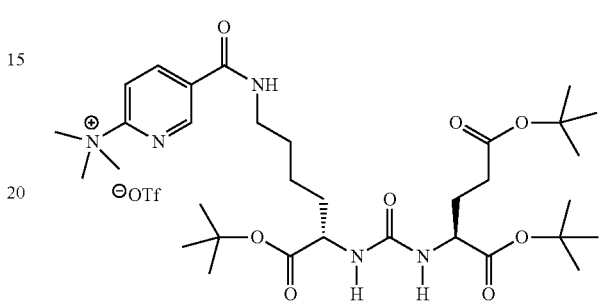

to the [$^{18}$F]fluoride ion from step (iii); and
   (v) heating the combined solution of step (iv).

28. The method of claim 27, wherein the heating of step (v) is performed at a temperature between 30° C. to 70° C.

29. The method of claim 27, wherein the heating of step (v) is performed for a period of time between 2 min to 10 min.

30. The method of claim 27, wherein the eluate of step (iii) comprising the [$^{18}$F]fluoride ion is dried at a temperature of between 80° C. to 150° C.

31. The method of claim 27, wherein the eluate of step (iii) comprising the [$^{18}$F]fluoride ion is dried under a nitrogen flow.

32. The method of claim 27, wherein the drying of step (iii) is performed for a period of time between 50 seconds to 300 seconds.

33. The method of claim 27, further comprising adding CH$_3$CN to the eluate of step (iii) comprising the [$^{18}$F]fluoride ion for further drying.

34. The method of claim 27, wherein the cartridge is preconditioned by washing with water prior to trapping [$^{18}$F]fluoride ion in the cartridge.

* * * * *